US012150819B2

(12) United States Patent
Hazelton et al.

(10) Patent No.: US 12,150,819 B2
(45) Date of Patent: *Nov. 26, 2024

(54) SYSTEM AND METHOD FOR IMAGE DETECTION DURING INSTRUMENT GRASPING AND STAPLING

(71) Applicant: INTUITIVE SURGICAL OPERATIONS, INC., Sunnyvale, CA (US)

(72) Inventors: Andrew J. Hazelton, San Carlos, CA (US); Ian E. McDowall, Woodside, CA (US); Theodore W. Rogers, Alameda, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/296,277

(22) Filed: Apr. 5, 2023

(65) Prior Publication Data
US 2023/0240789 A1 Aug. 3, 2023

Related U.S. Application Data

(63) Continuation of application No. 16/837,132, filed on Apr. 1, 2020, now Pat. No. 11,648,081.
(Continued)

(51) Int. Cl.
A61B 17/072 (2006.01)
A61B 17/295 (2006.01)
(Continued)

(52) U.S. Cl.
CPC .......... *A61B 90/361* (2016.02); *A61B 17/072* (2013.01); *A61B 17/07207* (2013.01);
(Continued)

(58) Field of Classification Search
CPC ......... A61B 1/015; A61B 1/042; A61B 1/043; A61B 1/0669; A61B 1/0684; A61B 1/12;
(Continued)

(56) References Cited

U.S. PATENT DOCUMENTS 5,383,880 A 1/1995 Hooven
5,503,320 A 4/1996 Webster et al.
(Continued)

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

Primary Examiner — Scott A Smith
(74) Attorney, Agent, or Firm — Artegis Law Group, LLP

(57) ABSTRACT

Systems and methods for image detection during grasping and stapling include an end effector having a first jaw and a second jaw, an imaging sensor mounted to the end effector and configured to capture images of a material graspable by the end effector, and one or more processors coupled to the end effector and the imaging sensor. The one or more processors are configured to receive the images from the imaging sensor, determine one or more properties of the material based on the images, and display the one or more properties of the material on an interface. In some embodiments, the end effector is part of a medical tool and the material is anatomical tissue. In some embodiments, the end effector further includes one or more of a stapling mechanism configured to staple the material or a cutting mechanism configured to cut the material.

20 Claims, 6 Drawing Sheets

Related U.S. Application Data

(60) Provisional application No. 62/828,289, filed on Apr. 2, 2019.

(51) Int. Cl.

| | | |
|---|---|---|
| *A61B 34/10* | (2016.01) | |
| *A61B 90/00* | (2016.01) | |
| *A61B 5/00* | (2006.01) | |
| *A61B 5/026* | (2006.01) | |
| *A61B 17/068* | (2006.01) | |
| *A61B 17/29* | (2006.01) | |
| *A61B 34/20* | (2016.01) | |
| *A61B 34/30* | (2016.01) | |
| *A61B 90/30* | (2016.01) | |

(52) U.S. Cl.
CPC ............ *A61B 17/295* (2013.01); *A61B 34/10* (2016.02); *A61B 5/0036* (2018.08); *A61B 5/0075* (2013.01); *A61B 5/0261* (2013.01); *A61B 17/068* (2013.01); *A61B 2017/07214* (2013.01); *A61B 2017/07271* (2013.01); *A61B 2017/07285* (2013.01); *A61B 2017/2929* (2013.01); *A61B 34/20* (2016.02); *A61B 34/30* (2016.02); *A61B 2090/306* (2016.02); *A61B 2090/373* (2016.02)

(58) Field of Classification Search
CPC .. A61B 1/128; A61B 1/04; A61B 1/06; A61B 17/068; A61B 17/0682; A61B 17/072; A61B 17/07207; A61B 17/115; A61B 17/00234; A61B 2017/00022; A61B 2017/07214; A61B 2017/2929; A61B 2017/2943; A61B 34/30; A61B 34/76
USPC .............. 227/19, 175.1, 175.2, 176.1, 180.1; 606/1, 139, 205, 219; 600/109, 112, 129, 600/156, 157, 173, 178, 179; 362/580, 362/800
See application file for complete search history.

(56) References Cited

U.S. PATENT DOCUMENTS

| | | |
|---|---|---|
| 5,562,239 A | 10/1996 | Boiarski et al. |
| 6,157,675 A | 12/2000 | Mitsuhashi et al. |
| 6,309,397 B1 | 10/2001 | Julian et al. |
| 6,648,816 B2 | 11/2003 | Irion et al. |
| 6,916,286 B2 | 7/2005 | Kazakevich |
| 8,622,896 B1 | 1/2014 | Termanini |
| 9,339,173 B2 | 5/2016 | McWeeney et al. |
| 10,548,679 B2* | 2/2020 | Carlson ................ A61B 34/70 |
| 10,813,700 B2* | 10/2020 | Amanatullah ........ A61B 90/361 |
| 10,861,197 B2* | 12/2020 | Kobayashi .............. G06T 7/149 |
| 11,100,631 B2* | 8/2021 | Yates .................... A61B 1/0669 |
| 11,109,866 B2* | 9/2021 | Shelton, IV ......... A61B 1/0661 |
| 11,304,692 B2* | 4/2022 | Scheib .................. A61B 34/30 |
| 11,648,081 B2* | 5/2023 | Hazelton .............. A61B 17/072 |
| | | 227/180.1 |
| 2001/0044578 A1 | 11/2001 | Ben-Haim et al. |
| 2005/0043718 A1 | 2/2005 | Madhani et al. |
| 2005/0240077 A1 | 10/2005 | Rovegno |
| 2008/0051632 A1 | 2/2008 | Ito et al. |
| 2008/0167672 A1 | 7/2008 | Giordano et al. |
| 2008/0208006 A1 | 8/2008 | Farr |
| 2008/0283570 A1 | 11/2008 | Boyden et al. |
| 2009/0024141 A1 | 1/2009 | Stahler et al. |
| 2010/0198009 A1 | 8/2010 | Farr et al. |
| 2011/0290855 A1 | 12/2011 | Moore et al. |
| 2013/0066304 A1 | 3/2013 | Belson et al. |
| 2014/0107496 A1 | 4/2014 | Hellstrom et al. |
| 2016/0213239 A1 | 7/2016 | Fujii |
| 2017/0086938 A1 | 3/2017 | Mak et al. |
| 2017/0231475 A1 | 8/2017 | McWeeney et al. |
| 2018/0020932 A1 | 1/2018 | Chen et al. |
| 2018/0271603 A1 | 9/2018 | Nir et al. |
| 2019/0029508 A1 | 1/2019 | Tabata et al. |
| 2019/0206050 A1 | 7/2019 | Yates et al. |
| 2019/0209080 A1 | 7/2019 | Gullotti et al. |
| 2020/0272660 A1 | 8/2020 | Wolf et al. |
| 2020/0289205 A1* | 9/2020 | Scheib .................... G01S 17/88 |
| 2020/0315735 A1 | 10/2020 | Hazelton et al. |
| 2021/0177370 A1 | 6/2021 | Robaina et al. |
| 2021/0196098 A1* | 7/2021 | Shelton, IV ........... A61B 1/045 |
| 2021/0196381 A1* | 7/2021 | Eckert ................ A61B 17/3205 |
| 2021/0196423 A1* | 7/2021 | Shelton, IV ......... A61B 90/361 |
| 2021/0196424 A1* | 7/2021 | Shelton, IV ........... A61B 34/25 |
| 2021/0307835 A1 | 10/2021 | Shelton, IV et al. |

* cited by examiner

SYSTEM AND METHOD FOR IMAGE DETECTION DURING INSTRUMENT GRASPING AND STAPLING

CROSS-REFERENCE TO RELATED APPLICATIONS

This application is a continuation of U.S. patent application Ser. No. 16/837,132, filed Apr. 1, 2020, now U.S. Pat. No. 11,648,081, which claims the benefit of U.S. Provisional Application No. 62/828,289, filed Apr. 2, 2019. Each of these application is incorporated by reference herein.

TECHNICAL FIELD

The present disclosure relates generally to operation of devices with imaging sensors and end effectors and more particularly to capturing images of end effectors during grasping, cutting, and/or stapling material.

BACKGROUND

More and more devices are being replaced with computer-assisted electronic devices. This is especially true in industrial, entertainment, educational, and other settings. As a medical example, the hospitals of today have large arrays of electronic devices in operating rooms, interventional suites, intensive care wards, emergency rooms, and/or the like. For example, glass and mercury thermometers are being replaced with electronic thermometers, intravenous drip lines now include electronic monitors and flow regulators, and traditional hand-held surgical and other medical instruments are being replaced by computer-assisted medical devices.

These computer-assisted devices are useful for performing operations and/or procedures on materials, such as the tissue of a patient. With many computer-assisted devices, an operator, such as a surgeon and/or other medical personnel, may typically manipulate input devices using one or more controls on an operator console. As the operator operates the various controls at the operator console, the commands are relayed from the operator console to a computer-assisted device located in a workspace where they are used to position and/or actuate one or more end effectors and/or tools that are mounted (e.g., via repositionable arms) to the computer-assisted device. In this way, the operator is able to perform one or more procedures on material in the workspace using the end effectors and/or tools. Depending upon the desired procedure and/or the tools in use, the desired procedure may be performed partially or wholly under control of the operator using teleoperation and/or under semi-autonomous control where the computer-assisted device may perform a sequence of operations based on one or more activation actions by the operator.

Computer-assisted devices, whether actuated manually, teleoperatively, and/or semi-autonomously may be used in a variety of operations and/or procedures and may have various configurations. Many such instruments include an end effector mounted at a distal end of a shaft that may be mounted to the distal end of a repositionable or articulated arm. In many operational scenarios, the shaft may be configured to be inserted into the workspace via an opening in the workspace. As a medical example, the shaft may be inserted (e.g., laparoscopically, thoracoscopically, and/or the like) through an opening (e.g., a body wall incision, a natural orifice, and/or the like) to reach a remote surgical site. In some instruments, an articulating wrist mechanism may be mounted to the distal end of the instrument's shaft to support the end effector with the articulating wrist providing the ability to alter an orientation of the end effector relative to a longitudinal axis of the shaft.

End effectors of different design and/or configuration may be used to perform different tasks, procedures, and functions so as to be allow the operator to perform any of a variety of procedures on a material. Examples include, but are not limited to, cauterizing, ablating, suturing, cutting, stapling, fusing, sealing, etc., and/or combinations thereof. Accordingly, end effectors can include a variety of components and/or combinations of components to perform these procedures.

In many embodiments, the size of the end effector is typically kept as small as possible while still allowing it to perform its intended task. One approach to keeping the size of the end effector small is to accomplish actuation of the end effector through the use of one or more inputs at a proximal end of the tool, which is typically located externally and/or peripherally to the workspace. Various gears, levers, pulleys, cables, rods, bands, and/or the like, may then be used to transmit actions from the one or more inputs along the shaft of the tool and to actuate the end effector. In some embodiments, a transmission mechanism at the proximal end of the tool interfaces with various motors, solenoids, servos, active actuators, hydraulics, pneumatics, and/or the like provided on a repositionable arm of the computer-assisted device. The motors, solenoids, servos, active actuators, hydraulics, pneumatics, and/or the like typically receive control signals through a master controller and provide input in the form of force and/or torque at the proximal end of the transmission mechanism, which the various gears, levers, pulleys, cables, rods, bands, and/or the like ultimately transmit to actuate the end effector at the distal end of the transmission mechanism.

Because of the remote nature of the operation of such end effectors, it may be difficult in some cases for the operator to directly monitor the end effector and/or grasping of the material. For example, in some cases, other portions of the computer-assisted device, including the end effector itself, other materials, and/or objects in the workspace may be hidden from view during the computer-assisted device's operation. In other cases it may be difficult to monitor and determine a presence or amount of material available to the end effector to perform a requested task (e.g., grasping, sealing, cutting, etc.). Variations in tissue availability and amount can often result in a grasping, clamping, and/or stapling operation with failed or incorrect operations due to material variations over space or time, and different steps of the operation such as the different stages of forcing staples through the material in a stapling operation.

Accordingly, improved methods and systems for the operation of computer-assisted devices, such as computer-assisted devices having end effectors used to grasp, seal, and/or cut a material are desirable. In some examples, it may be desirable to image areas proximate to the end effector during use of the computer-assisted device and the end effectors so as to help ensure that the tool may be able to successfully perform a desired procedure on the material.

SUMMARY

Consistent with some embodiments, a computer-assisted device includes an end effector having a first jaw and a second jaw, an imaging sensor mounted to the end effector and configured to capture one or more images of a material graspable by the end effector, and one or more processors coupled to the end effector and the imaging sensor. The one or more processors are configured to receive the one or more images from the imaging sensor, determine one or more properties of the material based on the one or more images, and display the one or more properties of the material on an interface.

Consistent with some embodiments, a method performed by one or more processors include operating an end effector having a first jaw and a second jaw, capturing one or more images of a material grasped by the end effector using an imaging sensor, determining one or more properties of the material based on the one or more images, and displaying information associated with the one or more properties on an interface with the one or more images. The information is associated with an amount of the material that is grasped by the end effector.

Consistent with some embodiments, non-transitory machine-readable medium comprising a plurality of machine-readable instructions which when executed by one or more processors are adapted to cause the one or more processors to perform any of the methods described herein.

Figure 1:
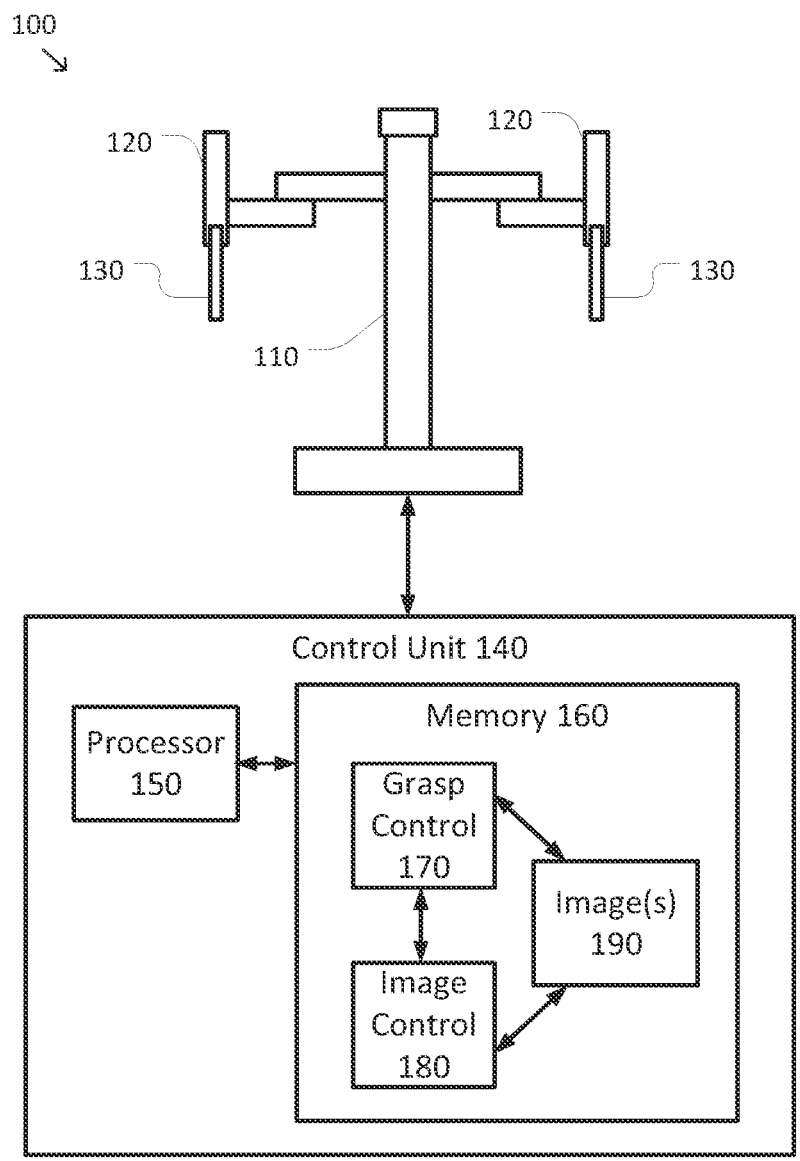
FIG. 1 is a simplified diagram of a computer-assisted system according to some embodiments.

In the Figures, elements having the same designations have the same or similar functions.

DETAILED DESCRIPTION

This description and the accompanying drawings that illustrate inventive aspects, embodiments, implementations, or modules should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Further, this description's terminology is not intended to limit the invention. For example, spatially relative terms-such as "beneath", "below", "lower", "above", "upper", "proximal", "distal", and the like-may be used to describe one element's or feature's relationship to another element or feature as illustrated in the figures. These spatially relative terms are intended to encompass different positions (i.e., locations) and orientations (i.e., rotational placements) of the elements or their operation in addition to the position and orientation shown in the figures. For example, if the content of one of the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes include various special element positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements described in detail with reference to one embodiment, implementation, or module may, whenever practical, be included in other embodiments, implementations, or modules in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

In some instances, well known methods, procedures, components, and circuits have not been described in detail so as not to unnecessarily obscure aspects of the embodiments.

This disclosure describes various devices, elements, and portions of computer-assisted devices and elements in terms of their state in three-dimensional space. As used herein, the term "position" refers to the location of an element or a portion of an element in a three-dimensional space (e.g., three degrees of translational freedom along Cartesian x-, y-, and z-coordinates). As used herein, the term "orientation" refers to the rotational placement of an element or a portion of an element (three degrees of rotational freedom—e.g., roll, pitch, and yaw). As used herein, the term "shape" refers to a set positions or orientations measured along an element. As used herein, and for a device with repositionable arms, the term "proximal" refers to a direction toward the base of the computer-assisted device along its kinematic chain and "distal" refers to a direction away from the base along the kinematic chain.

Aspects of this disclosure are described in reference to computer-assisted systems and devices, which may include systems and devices that are teleoperated, remote-controlled, autonomous, semiautonomous, robotic, and/or the like. Further, aspects of this disclosure are described in terms of an implementation using a surgical system, such as the da Vinci® Surgical System commercialized by Intuitive Surgical, Inc. of Sunnyvale, California. Knowledgeable persons will understand, however, that inventive aspects disclosed herein may be embodied and implemented in various ways, including robotic and, if applicable, non-robotic embodiments and implementations. Implementations on da Vinci® Surgical Systems are merely exemplary and are not to be considered as limiting the scope of the inventive aspects disclosed herein. For example, techniques described with reference to surgical instruments and surgical methods may be used in other contexts. Thus, the instruments, systems, and methods described herein may be used for humans, animals, portions of human or animal anatomy, industrial systems, general robotic, or teleoperational systems. As further examples, the instruments, systems, and methods described herein may be used for non-medical purposes including industrial uses, general robotic uses, sensing or manipulating non-tissue work pieces, cosmetic improvements, imaging of human or animal anatomy, gathering data from human or animal anatomy, setting up or taking down systems, training medical or non-medical personnel, and/or the like. Additional example applications include use for procedures on tissue removed from human or animal anatomies (without return to a human or animal anatomy) and for procedures on human or animal cadavers. Further, these techniques can also be used for medical treatment or diagnosis procedures that include, or do not include, surgical aspects.

FIG. 1 is a simplified diagram of a computer-assisted system 100 according to some embodiments. As shown in FIG. 1, computer-assisted system 100 includes a device 110 with one or more repositionable arms 120. Each of the one or more repositionable arms 120 may support one or more tools 130. In some examples, device 110 may be consistent with a computer-assisted medical device. The one or more tools 130 may include tools, imaging devices, and/or the like. In some medical examples, the tools may include medical tools, such as clamps, grippers, retractors, cautery tools, suction tools, suturing devices, and/or the like. In some medical examples, the imaging devices may include endoscopes, cameras, ultrasonic devices, fluoroscopic devices, and/or the like. In some examples, each of the one or more tools 130 may be inserted into a workspace (e.g., anatomy of a patient, a veterinary subject, and/or the like) through a respective cannula mounted to a respective one of the one or more repositionable arms 120. In some examples, a direction of view of an imaging device may correspond to an insertion axis of the imaging device and/or may be at an angle relative to the insertion axis of the imaging device. In some examples, each of the one or more tools 130 may include an end effector that may include an imaging sensor (e.g., a camera or other radiation detection component of the end effector). The end effector may be capable of capturing an image of a scene at and/or nearby the end effector using the imaging sensor, such as a scene proximate to a distal tip of the end effector and/or between a space created by the end effector and/or portions of the end effector. In some examples, the end effector may further be capable of grasping a material (e.g., tissue of a patient) located in the workspace prior to, during, and/or after capturing one or more images. The imaging sensor may determine properties of the material prior to, during, and/or after grasping the material, which may be used to determine a percentage of the end effector filled with the material prior to, during, and/or after the grasping the material. In some embodiments, computer-assisted system 100 may be found in an operating room and/or an interventional suite.

Device 110 is coupled to a control unit 140 via an interface. The interface may include one or more cables, connectors, and/or buses and may further include one or more networks with one or more network switching and/or routing devices. Control unit 140 includes a processor 150 coupled to memory 160. Operation of control unit 140 is controlled by processor 150. And although control unit 140 is shown with only one processor 150, it is understood that processor 150 may be representative of one or more central processing units, multi-core processors, microprocessors, microcontrollers, digital signal processors, field programmable gate arrays (FPGAs), application specific integrated circuits (ASICs), graphics processing units (GPUs), tensor processing units (TPUs), and/or the like in control unit 140. Control unit 140 may be implemented as a stand-alone subsystem and/or as a board added to a computing device or as a virtual machine.

Memory 160 may be used to store software executed by control unit 140 and/or one or more data structures used during operation of control unit 140. Memory 160 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown, memory 160 includes a grasp control module 170, an image control module 180, and one or more images 190, that may be used to control, monitor, and/or provide properties associated with one of the one or more of tools 130 as is described in further detail below. And although FIG. 1 shows grasp control module 170, image control module 180, and the one or more images 190 as separate elements stored within a same memory 160 of a same control unit 140, other configurations are possible. In some examples, grasp control module 170, image control module 180, and the one or more images 190 may be combined partially and/or completely within a same module. In some examples, grasp control module 170, image control module 180, and the one or more images 190 may alternatively be stored in different memories, and/or associated with different control units. Further, even though grasp control module 170, image control module 180, and the one or more images 190 are characterized as software modules, each may be implemented using software, hardware, and/or a combination of hardware and software.

In some embodiments, grasp control module 170 is responsible for managing the mechanical operation of the one or more tools 130. In some examples, grasp control module 170 may monitor one or more sensors used to track the position, orientation, articulation, and/or mechanical actuation of the one or more tools 130 and their respective end effectors and/or one or more material properties of material being interacted with by the one or more tools 130 and their respective end effectors. In some examples, grasp control module 170 may control the position, orientation, articulation, and/or mechanical actuation of the one or more tools 130 and their respective end effectors using one or more actuators based on the monitoring and/or the one or more images 190. In some examples, control of the position, orientation, articulation, and/or mechanical actuation of the one or more tools 130 and their respective end effectors may include controlling one or more degrees of freedom including, as examples, an insertion depth, a roll, a pitch, a yaw, a wrist articulation, an angle between jaws, a force or torque applied, and/or the like.

In some embodiments, image control module 180 is responsible for managing an imaging sensor, device, and/or camera attached to or associated with of the one or more tools 130. In some examples, image control module 180 may monitor one or more imaging sensors used to capture images of scenes at and/or proximate to the one or more of tools 130 and/or track a location of the one or more tools 130 and their respective end effectors. In some examples, image control module 180 may determine one or more material properties of materials being interacted with by the one or more tools 130 and/or their respective end effectors. In some examples, image control module 180 may control the energy delivered by an illuminating source, such as an infrared and/or visible light source, associated with the one or more imaging sensors using one or more light sources, illumination systems, signal generators, optical fibers, and/or the like, which may be utilized during the use of the imaging sensor to capture the one or more images 190.

In some embodiments, the one or more images 190 include visual image data and accompanying properties determined using the visual image data during the use of grasp control module 170 and/or image control module 180 to control mechanical and/or energy movement and delivery, respectively, of the one or more tools 130 and their respective end effectors. In some examples, the one or more images 190 may include one or more still images, videos (e.g., a collection of still images in a sequence), and/or the like, which may be captured by the imaging sensor attached and/or associated with the one or more tools 130 and/or their respective end effectors as is described in further detail below. In some examples, one or more properties may be determined from the one or more images, such as properties of the material grasped and/or graspable by the one or more tools 130 and/or their respective end effectors. In some examples, the one or more properties may include a desiccation of the material, a presence or absence of the material grasped and/or graspable by the one or more tools 130 and/or their respective end effectors, a pressure applied to the material, a transmissivity of the material and/or moisture within and/or in contact with the material, a fluorescence of the material, a length of fill of a space between the one or more tools 130 and/or their respective end effectors, and/or the like, and may include a change in the aforementioned properties.

In some examples, the one or more properties of the one or more images 190 may be used to determine and/or estimate further data within the one or more images 190, including a percentage fill of a grasping mechanism of the one or more tools 130 and/or their respective end effectors. In some embodiments, image control module 180 may also be responsible for providing orientation hints and/or visual clues that may be output through an interface that informs an operator of an orientation of the one or more tools 130 and/or their respective end effectors within a workspace using the one or more images 190 and/or their corresponding properties. For example, image control module 180 may provide an image, representation, and/or indication of a view of the one or more tools 130 and/or their respective end effectors within a workspace, which may be used with, prior to, and/or overlaid on the one or more images to provide the orientation hints. In some examples, image control module 180 may orient the view of an imaging sensor attached to and/or associated with the one or more tools 130 and their respective end effectors relative to one or more axes of the workspace. In some embodiments, image control module 180 may provide an animation of the orientation hints prior to, during, and/or after display of the one or more images 190, such as an animation of a T-pose of a body in a prone position that is animated to display entrance of the one or more tools 130 and/or their respective end effectors to a workspace (e.g., the body of a patient).

In some embodiments, image control module 180 may also provide video stabilization to the one or more images constituting a video during use and/or movement of the one or more tools 130 and their respective end effectors. For example, image control module 180 may fix relative points within a workspace to relative locations within an interface during the use and/or movement of the one or more tools 130 and/or their respective end effectors. Thus, image control module 180 may apply one or more image/video stabilization algorithms utilizing the fixed points to adjust for the use and/or movement of the one or more tools 130 and/or their respective end effectors and/or other destabilizing events from the workspace. For example, fixed points in tissue of a patient may be relatively fixed to locations within an interface to provide for such image/video stabilization during use and/or movement of the one or more tools 130 and/or their respective end effectors.

As discussed above and further emphasized here, FIG. 1 is merely an example which should not unduly limit the scope of the claims. One of ordinary skill in the art would recognize many variations, alternatives, and modifications. According to some embodiments, computer-assisted system 100 may include any number of computer-assisted devices with articulated arms and/or instruments of similar and/or different in design from computer-assisted device 110. In some examples, each of the computer-assisted devices may include fewer or more articulated arms and/or instruments.

According to some embodiments, the arrangement of grasp control module 170, image control module 180, and/or the one or more images 190 may be different than as depicted in FIG. 1. In some examples, grasp control module 170, image control module 180, and/or the one or more images 190 may be distributed across more than one control unit. In some examples, grasp control module 170 and image control module 180 may be included in a single control module. In some examples, the one or more images 190 may be included in grasp control module 170 and/or image control module 180.

Figure 2:
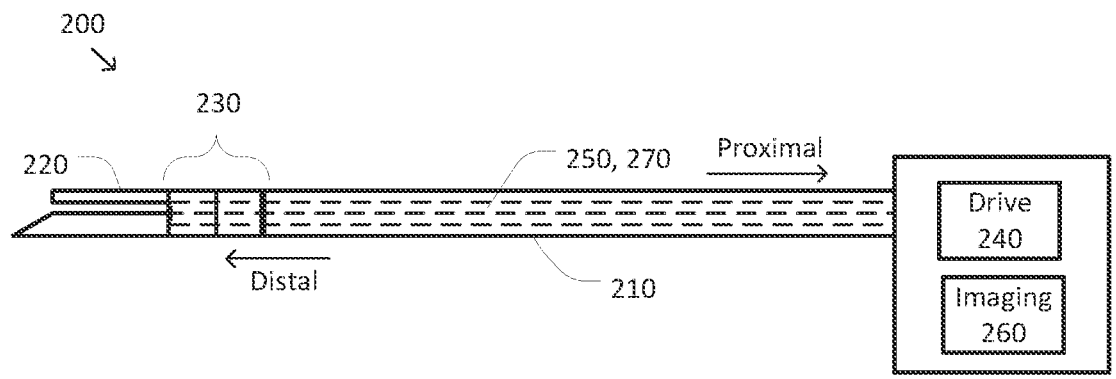
FIG. 2 is a simplified diagram showing a tool suitable for use with the computer-assisted system of FIG. 1 according to some embodiments.

FIG. 2 is a simplified diagram showing a tool 200 suitable for use with the computer-assisted system 100 according to some embodiments. In some embodiments, tool 200 may be consistent with any of the tools 130 of FIG. 1. The directions "proximal" and "distal" as depicted in FIG. 2 and as used herein help describe the relative orientation and location of components of tool 200.

As shown in FIG. 2, tool 200 includes a long shaft 210 used to couple an end effector 220 located at a distal end of shaft 210 to where the tool 200 is mounted to a repositionable arm and/or a computer-assisted device at a proximal end of shaft 210. Depending upon the particular procedure for which the tool 200 is being used, shaft 210 may be inserted through an opening (e.g., a body wall incision, a natural orifice, and/or the like) in order to place end effector 220 in proximity to a workspace, such as a remote surgical site located within the anatomy of a patient. As further shown in FIG. 2, end effector 220 is generally consistent with a two-jawed gripper-style end effector, which in some embodiments may further include an imaging sensor and/or image capture mechanism as is described in further detail below with respect to FIGS. 3A, 3B, 4A, 4B, 5, 6A, 6B, and/or 6C. However, one of ordinary skill would understand that different tools 200 with different end effectors 220 are possible and may be consistent with the embodiments of tool 200 as described elsewhere herein.

A tool, such as tool 200 with end effector 220 typically relies on multiple degrees of freedom (DOFs) during its operation. Depending upon the configuration of tool 200 and the repositionable arm and/or computer-assisted device to which it is mounted, various DOFs that may be used to position, orient, and/or operate end effector 220 are possible. In some examples, shaft 210 may be inserted in a distal direction and/or retreated in a proximal direction to provide an insertion DOF that may be used to control how deep within the workspace end effector 220 is placed. In some examples, shaft 210 may be able rotate about its longitudinal axis to provide a roll DOF that may be used to rotate end effector 220. In some examples, additional flexibility in the position and/or orientation of end effector 220 may be provided by an articulated wrist 230 that is used to couple end effector 220 to the distal end of shaft 210. In some examples, articulated wrist 230 may include one or more rotational joints, such as one or more roll, pitch or yaw joints that may provide one or more "roll," "pitch," and "yaw" DOF(s), respectively, that may be used to control an orientation of end effector 220 relative to the longitudinal axis of shaft 210. In some examples, the one or more rotational joints may include a pitch and a yaw joint; a roll, a pitch, and a yaw joint, a roll, a pitch, and a roll joint; and/or the like. In some examples, end effector 220 may further include a grip DOF used to control the opening and closing of the jaws of end effector 220. Depending upon the configuration, end effector 220 may include two moveable jaws that are articulated with respect to each other about a hinge point located near a proximal end of end effector 220 or one fixed jaw and one moveable jaw that is articulated with respect to the fixed jaw about the hinge point. End effector 220 may also include an activation DOF used to control the extension, retraction, and/or operation of a stapling and cutting mechanism as is described in further detail below.

Tool 200 further includes a drive system 240 located at the proximal end of shaft 210. Drive system 240 includes one or more components for introducing forces and/or torques to tool 200 that may be used to manipulate the various DOFs supported by tool 200. In some examples, drive system 240 may include one or more motors, solenoids, servos, active actuators, hydraulic actuators, pneumatic actuators, and/or the like that are operated based on signals received from a control unit, such as control unit 140 of FIG. 1. In some examples, the signals may include one or more currents, voltages, pulse-width modulated wave forms, and/or the like. In some examples, drive system 240 may include one or more shafts, gears, pulleys, rods, bands, and/or the like which may be coupled to corresponding motors, solenoids, servos, active actuators, hydraulics, pneumatics, and/or the like that are part of the articulated arm, such as any of the repositionable arms 120, to which tool 200 is mounted. In some examples, the one or more drive inputs, such as shafts, gears, pulleys, rods, bands, and/or the like, may be used to receive forces and/or torques from the motors, solenoids, servos, active actuators, hydraulics, pneumatics, and/or the like and apply those forces and/or torques to adjust the various DOFs of tool 200.

In some embodiments, the forces and/or torques generated by and/or received by drive system 240 may be transferred from drive system 240 and along shaft 210 to the various joints and/or elements of tool 200 located distal to drive system 240 using one or more drive mechanisms 250. In some examples, the one or more drive mechanisms may include one or more gears, levers, pulleys, cables, rods, bands, and/or the like. In some examples, shaft 210 is hollow and drive mechanisms 250 pass along the inside of shaft 210 from drive system 240 to the corresponding DOF in end effector 220 and/or articulated wrist 230. In some examples, each of drive mechanisms 250 may be a cable disposed inside a hollow sheath or lumen in a Bowden cable like configuration. In some examples, the cable and/or the inside of the lumen may be coated with a low-friction coating such as polytetrafluoroethylene (PTFE) and/or the like. In some examples, as the proximal end of each of the cables is pulled and/or pushed inside drive system 240, such as by wrapping and/or unwrapping the cable about a capstan or shaft, the distal end of the cable moves accordingly and applies a suitable force and/or torque to adjust one of the DOFs of end effector 220, articulated wrist 230, and/or tool 200. In some examples, drive system 240 may be controlled and/or receive instructions from a grasp control module, such as grasp control module 170.

In some embodiments, tool 200 further includes an imaging system 260 located at the proximal end of shaft 210. Imaging system 260 includes one or more components for capturing one or more images, including video, using an imaging sensor attached to and/or associated with tool 200. In some examples, the imaging sensor may be capable of capturing visual images and/or video of a scene at and/or proximate to the end effector 220 located at the distal end of shaft 210. In some embodiments, imaging system 260 may also and/or alternatively be capable of capturing other types of signals and/or radiation including ultrasonic, radio frequency, electrical, magnetic, thermal, light, and/or the like. In some examples, imaging system 260 may include one or more illumination systems that may apply illumination to a scene, such as visible light (e.g., white and/or colored light), infrared light/radiation, and/or the like. In some embodiments, imaging system 260 may also include components used by an image control module, such as image control module 180, to determine one or more properties of a material from the one or more images and accompanying data (e.g., a percentage fill of a two-jawed gripper-style end effector with material and/or orientation hints for an orientation of tool 200 in a workspace), as well as provide additional features (e.g., fixed point detection on a material for image/video stabilization).

In some embodiments, the one or more images captured by an imaging sensor located at end effector 220 and distal to imaging system 260 may be transferred from the imaging sensor and along shaft 210 to imaging system 260 using one or more image delivery mechanisms 270. In some examples, the one or more image delivery mechanisms 270 may include one or more wires, cables, optical fibers, and/or like. In some examples, shaft 210 is hollow and image delivery mechanisms 270 pass along the inside of shaft 210 from imaging system 260 to end effector 220. Image delivery mechanism 270 therefore assist in data exchange when capturing one or more images of a scene of a material within the workspace by imaging system 260 using the distally located imaging sensor at end effector 220. In some examples, imaging system 260 may be controlled and/or receive instructions from an image control module, such as image control module 180.

Figure 3A:
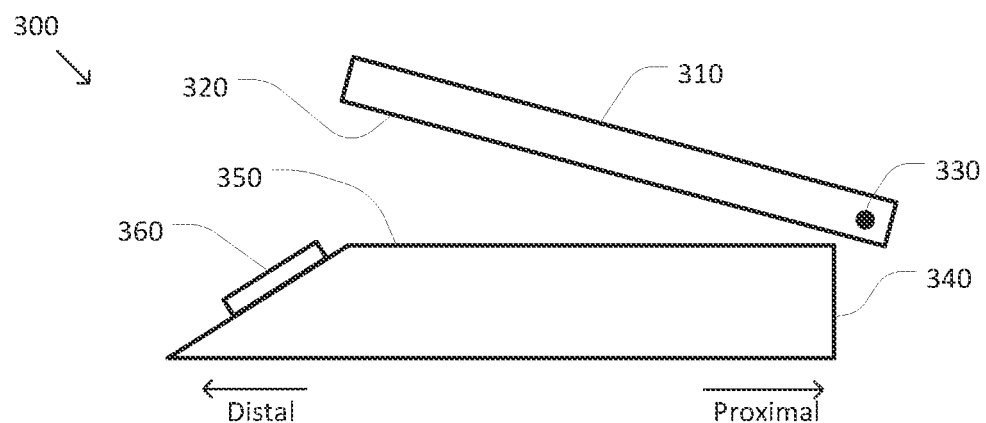
FIGS. 3A and 3B are simplified side and surface views of an end effector of a tool having a distal tip mounted imaging sensor according to some embodiments.
Figure 3B:
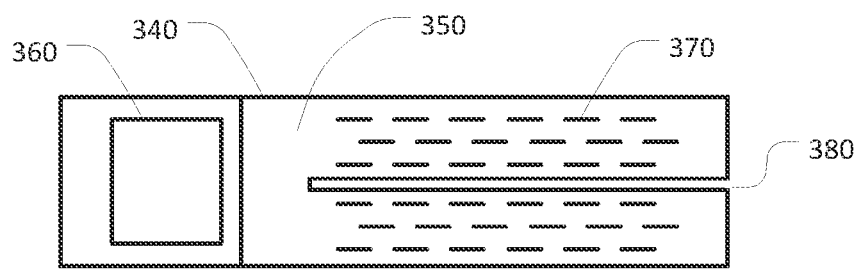

FIGS. 3A and 3B are simplified side and top views of an end effector 300 of a tool according to some embodiments. In some embodiments, end effector 300 is consistent with either or both of the jaws of end effector 220. As shown in FIGS. 3A and 3B, end effector 300 is located at the distal end of tool 200 (e.g., end effector 220) and includes a mechanism for jaw closure, tissue stapling, and tissue cutting. And although end effector 220 is shown and described with one fixed and one movable jaw, one of ordinary skill would understand that the distal end of tool 200 could be modified to use two movable jaws. It should be further understood that although the description below is in the context of a grasping, stapling, and cutting instrument that simultaneously grasps, staples, and cuts tissue, the aspects so described may be applicable to instruments with or without cutting features, instruments supporting fusing rather than stapling, and/or the like.

As shown in FIG. 3A, end effector 300 shows a cut-way side view of end effector 220 prior to actuation so that the jaws of end effector 220 are shown in an open position. As shown, end effector includes a first jaw 340 that is generally fixed. As further shown in FIG. 3A, end effector 300 of end effector 220 further includes a second jaw 310 that is movable about a pivot point 330 near its proximal end. In the context of a stapling instrument, second jaw 310 may alternatively be referred to as anvil 310. In some embodiments, pivot point 330 is configured so that upon initial actuation of end effector 220, a gap between first jaw 340 and second jaw 310 is rapidly reduced until a material is grasped between first jaw 340 and second jaw 310. Actuation of end effector 220 is accomplished by grasp control module 170 with drive system 240 from the proximal end of end effector 220 providing mechanical actuation, electrical signals, and/or the like to the distal end of end effector 220. Thus, one or more components of end effector 300 are coupled to one or more of the drive mechanisms 250. First jaw 340 further includes a first jaw surface 350 and second jaw 310 further includes a second jaw surface 320. In some examples, second jaw surface 320 is generally planar and is parallel with first jaw surface 350 of first jaw 340 when end effector 300 is closed relative to the opposing jaws. Thus, second jaw surface 320 is at an angle to first jaw surface 350 when end effector 300 is open. As shown, end effector 300 may be utilized for grasping, cutting, and/or stapling effects when pivoted around pivot point 330.

In FIG. 3A, end effector 300 further includes an imaging sensor 360 that may capture images of a scene at and/or in proximity to end effector 300 during use, movement, and/or actuation of end effector 300. Imaging sensor 360 may correspond to a sensor capable of capturing still images and/or video of a scene, such as a sensor array having one or more sensor pixels arranged in array or other fashion that is capable of detecting incident radiation on the sensor pixel. In some embodiments, imaging sensor 360 may be capable of capturing visual images at and/or nearby tool 200 using visible light. In such embodiments, imaging sensor 360 may correspond to a charge-coupled device (CCD) and/or complementary metal-oxide semiconductor (CMOS) image sensor. Imaging sensor 360 may correspond to a rectangular imaging sensors (e.g., a 400×400 array), which may include a regular or wide angle lens, able to capture an image at a point in time based on incoming radiation. Imaging sensor 360 may also correspond to a single line of sensors that may reconstruct an image over time based on movement of end effector 220. However in further embodiments, imaging sensor 360 may also and/or alternatively include a thermal and/or infrared sensor that may be capable of capturing infrared images of the scene. Imaging using imaging sensor 360 on end effector 220 is accomplished by image control module 180 with imaging system 260 from the proximal end of end effector 220 exchanging electrical signals and the like with imaging sensor 360. Thus, one or more components of imaging sensor 360 are coupled to the one or more of the image delivery mechanisms 270. It should be further understood that although the description below is in the context of an image sensor instrument that captures visual images and/or infrared images, the aspects so described may be applicable to instruments with other types of sensors capable of capturing other types of radiation and/or the like.

In some embodiments, imaging sensor 360 and/or another component of end effector 300 may include an illumination or lighting system (not shown), which may provide illumination to the scene to be captured using imaging sensor 360. In such embodiments, an emitter may be located with, at, and/or proximate to imaging sensor 360 to provide the illumination, and may correspond to a light emitting diode (LED), light pipe, luminescent and/or leaky optical fiber that emits light, and/or the like. The illumination may correspond to visible light, such as colored or white light, which may be used to illuminate the scene during capture of visual images. The illumination may also correspond to non-visible light, such as infrared light and/or the like, which may provide fluorescence of a scene, infrared imaging, and/or the like. The illumination system may further include a transmission system through tool 200 (e.g., from one or more modules/systems located at the proximal end of tool 200 to the distal end of tool 200), which may be incorporated with the one or more of the image delivery mechanisms 270. The transmission system may include one or more optical fibers that transmit the illuminating light to end effector 220 from a light source at the proximal end of tool 200. In some embodiments, the light source may correspond to a light engine having red, green, and blue LEDs and/or laser diodes that may mix to create colored/white light, a white LED, an infrared light source, an ultraviolet light source, and/or the like. In some examples, an imaging system, such as imaging system 260 (and/or in conjunction with image control module 180) may be used to control the illumination amount, cycles, and/or limits applied to the illumination system. For example, in order to reduce and/or avoid incident heat on a scene, the imaging system may monitor, control, and/or reduce illumination as necessary to avoid unwanted heating of the scene. In some embodiments, the illumination emitter may be located on one or more of first jaw 340 and/or second jaw 310, or may be located elsewhere, such as on an endoscope associated with end effector 300 and located proximate to imaging sensor 360 so that illumination may be provided to the scene.

In FIG. 3B a second orientation of end effector 300 is shown, where second jaw 310 is removed and a top down view of first jaw surface 350 of first jaw 340 is shown. In some embodiments, imaging sensor 360 is located on first jaw 340, such as on an offset surface, flange, or area that allows imaging sensor 360 to view, at an upward angle and/or degree, end effector 300 of end effector 220, such as a space or area between first jaw surface 350 and second jaw surface 320. Thus, imaging sensor 360 may correspond to a forward looking sensor capable of imaging in front of end effector 220, an imaging sensor perpendicular to first jaw 340 and/or second jaw 310 capable of imaging an area or space between first jaw surface 350 and second jaw surface 320, and/or a combination of the two. Imaging sensor 360 is shown near distal tip of end effector 220 so as to provide imaging of the immediate area at and/or around end effector 300 of end effector 220. Imaging sensor 360 is therefore shown to be opposite second jaw 310 to allow for imaging of an area between first jaw 340 and second jaw 310, such as a material within an area between first jaw surface 350 and second jaw surface 320 that is captured and/or grasped. In some embodiments, imaging sensor 360 may also and/or alternatively be located on or at second jaw 310, so that imaging sensor 360 may also and/or alternatively be opposite first jaw 340. This allows for direct viewing of first jaw surface 350 and/or determination of the material in the area between first jaw surface 350 and second jaw surface 320. However, it should be further understood that although the description below is in the context of an image sensor instrument near the distal tip of an end effector, the aspects so described may be applicable to instruments with other placements of an imaging sensor along a tool and/or along an end effector.

In some embodiments of FIG. 3B, first jaw 340 is designed to receive a replaceable staple cartridge holding a plurality of staples and a plurality of staple pushers. FIG. 3B shows a top view of first jaw surface 350 having six rows of staple slots 370 through which the staples may be applied to grasped tissue upon actuation of end effector 220. The rows of staple slots 370 include three rows on each side of a cutting slot 380. A cutting blade may be located somewhat proximally to the distal ends of end effector 300 so that cutting of any grasped tissue trails the firing of the staples along both sides of the cutting line of cutting slot 380. As a cutting blade is actuated, the cutting blade travels along cutting slot 380 as well as a corresponding cutting slot located in second jaw 310.

Placing the staples on both sides of cutting slot 380 allows for the application of the staples to both sides of a desired cutting line so as to close the tissue on both sides of the cutting line. The rows of staple slots 370 are also offset relative to each other to provide more complete tissue closure along both sides of the cutting line. And although, FIG. 3B is shown with six rows of offset staple slots 370, each having six staple slots 370 of uniform size, one of ordinary skill would understand that fewer or more rows of staple slots with fewer or more staples, staple slots of varying size, and staple slots of varying patterns are possible. In some embodiments, the staple cartridge providing the staples is designed to be replaceable so that end effector 220 is reusable by removing a first staple cartridge after one or more of the staples are used and replacing it with a second staple cartridge having a new set of staples that can be used to further perform the surgical procedure.

In some embodiments, when imaging using imaging sensor 360, one or more images, such as one or more of images 190, may be captured of a space and/or an area between first jaw surface 350 and second jaw surface 320. The area may correspond to an area that is graspable and/or grasped by first jaw 340 and second jaw 310 during use of end effector 220. Thus, the one or more images 190 may be used to estimate and/or determine an amount of the area that is filled with material in the workspace (e.g., tissue of a patient when performing a grasping and/or stapling event during a medical use or operation). In some embodiments, imaging sensor 360 may include a field of vision that allows imaging sensor 360 to image an entire scene between first jaw surface 350 and second jaw surface 320, and/or a substantial portion of the scene. In some embodiments, imaging sensor 360 may capture the image as first jaw 340 and second jaw 310 move into position to grasp a material, and may continue to capture and/or alternatively capture one or more images after grasping the material. The images may therefore present an amount and/or presence of the material occupying the area or space between first jaw surface 350 and second jaw surface 320. Imaging sensor 360 may be located at, along, or nearby first jaw 340 and/or second jaw 310 in order to provide imaging of the space through one or more images captured from their respective point of views.

Thus, a percentage fill of the space and/or area between first jaw surface 350 and second jaw surface 320 may be approximated based on the visible material (e.g., tissue) between first jaw surface 350 and second jaw surface 320. Utilizing the percentage fill of the space between first jaw surface 350 and second jaw surface 320, an amount of the material that is grasped and/or graspable may be determined for use in performing the grasping, cutting, and/or stapling actions described above for end effector 220. The percentage fill may correspond to a percentage occupancy of the material in the space between first jaw surface 350 and second jaw surface 320, an amount or volume of the material, and/or another metric to measure the material that is grasped or graspable by end effector 220 (e.g., using first jaw 340 and second jaw 310). Light may be provided by an illumination system in order to view and/or better illuminate the space between first jaw surface 350 and second jaw surface 320 so that the amount and/or percentage of the space that is filled with the material may be better determined. Imaging sensor 360 may be located near the distal tip of one or more of first jaw 340 and/or second jaw 310 in order to provide imaging around an object in an environment or workplace, such as around tissue when operating within a patient. In some embodiments, imaging sensor 360 may also and/or alternatively correspond to a forward-looking imaging sensor that captures images of the material or structures prior to and/or during entry in the area and/or space between first jaw surface 350 and second jaw surface 320. In some embodiments, imaging sensor 360 may also provide imaging and/or analysis of normally hidden objects when located at the distal tip of end effector 220.

In some embodiments, imaging sensor 360 may additionally be used to determine additional properties of the material at and/or nearby end effector 220 using the one or more images captured by imaging sensor 360, such as a material grasped and/or graspable between first jaw surface 350 and second jaw surface 320. For example, where imaging sensor 360 corresponds to and/or includes an infrared sensor, a desiccation level and/or amount of the tissue may be determined prior to and/or during grasping the material. In some embodiments, imaging sensor 360 may utilize specific wavelengths of light, such as at 1600 nm, 3500 nm, and/or another wavelength at which water absorbs and/or transmits light (e.g., better than other relative wavelengths) to determine the desiccation level of the material. For example, in certain states (e.g., temperature, solid/liquid/gaseous phase) water may better absorb or transmit light through the medium (e.g., the current state of the water particles), than at other wavelengths so as to provide better absorption and/or transmittance of radiation through the particular medium. Radiation may be better absorbed or transmitted such that a detector array may determine the relative amount or level (e.g., desiccation level) of the water based on the amount of radiation transmitted through the material and/or medium. A first wavelength may therefore be better absorbed or transmitted through and/or by a material or medium of the liquid that is more strongly or weakly absorbed or transmitted by that material and/or medium. Thus, various states of the water may strongly or weakly absorb and/or transmit radiance that is incident through the particles.

Desiccation of the material (e.g., tissue) may occur prior to and/or during a grasping action by end effector 300. When a grasping event occurs, liquid (e.g., water) may be desiccated from the material (e.g., tissue). In such embodiments, by viewing the amount of light at each pixel, a water content and/or desiccation of the material may be determined, and/or a state of compression of the material may be identified by the imaging system. When utilizing more than one wavelength, such as a wavelength at which water absorbs and another where water transmits, the imaging system may utilize a ratio of detected radiation at each wavelength to more sensitively detect a presence of water and/or other fluid with the material. In some embodiments, imaging sensor 360 may also be used to determine the presence of other fluids, such as blood, other bodily fluids, and/or the like during a medical operation, which may be utilized to assist in actions by end effector 220 and diagnosis of issues within a workspace (e.g., a patient). In some embodiments, imaging sensor 360 may also be used to determine a fluorescence of a material using one or more wavelengths of light to determine material type, desiccation, and/or other property. For example, 800 nm light may be used to trigger fluorescence in tissue. When determining such properties, imaging sensor 360 may provide the one or more images and/or other data to an imaging system, such as imaging system 260, which may process the images using one or more modules, such as image control module 180.

As discussed above and further emphasized here, FIGS. 3A and 3B are merely examples which should not unduly limit the scope of the claims. One of ordinary skill in the art would recognize many variations, alternatives, and modifications. According to some embodiments, a relative size of the surface areas of the one or more of first jaw surface 350, second jaw surface 320, and/or imaging sensor 360 may be different than as depicted in FIGS. 3A and 3B. According to some embodiments, the relative height, placement location, orientation, and/or field of vision of imaging sensor 360 may be different than as depicted in FIGS. 3A and 3B. In some examples, imaging sensor 360 may be flush with first jaw 340 and/or recessed below first jaw 340. In some embodiments, an axial length (from proximal to distal) along end effector 300 of imaging sensor 360 may be longer, shorter, and/or of different lengths.

According to some embodiments, control of an end effector, such as end effector 220, that supports both grasping (e.g., using opposing jaws) and image capture and delivery (e.g., using imaging sensor 360) are typically controlled using separate systems. For example, a drive system and a corresponding grasp control module may control the grasping while an imaging system and a corresponding image control module may control the image capture, delivery, and/or processing. In some examples, there may be little or no cooperation between drive system/grasp control module and the imaging system/image control module. That is, the drive system/grasp control module may control grasping based on mechanical and/or kinematic properties of the grasped material and not the material and spatial occupancy properties of the grasped material that indicate whether grasping, sealing, and/or cutting are occurring satisfactorily. Similarly, the imaging system/image control module may control imaging and image display based on material and spatial occupancy properties of the grasped material and not the mechanical and/or kinematic properties of the material that indicate whether a grasp of the material that is likely to result in good grasping, sealing, and/or cutting has been obtained. Accordingly, better sealing and cutting of a grasped material may be obtained when the drive system/grasp control module and the imaging system/image control module work together to control both the grasping and imaging so that both the grasping and imaging work to complement each other.

Figure 4A:
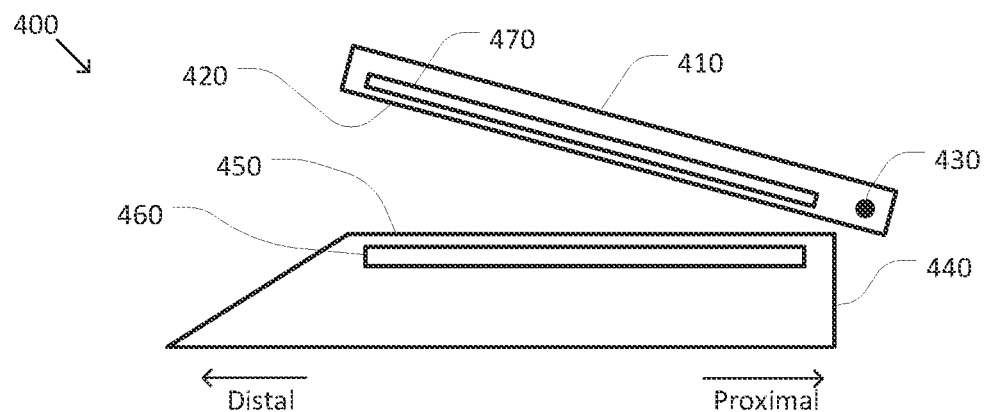
FIGS. 4A and 4B are simplified side and surface views of an end effector of a tool having a side jaw mounted imaging sensor according to some embodiments.
Figure 4B:
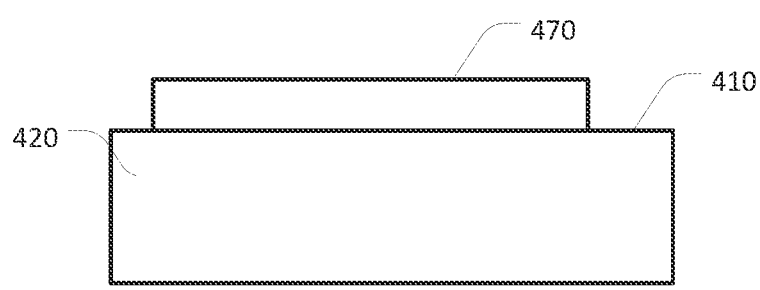
Figure 4B:
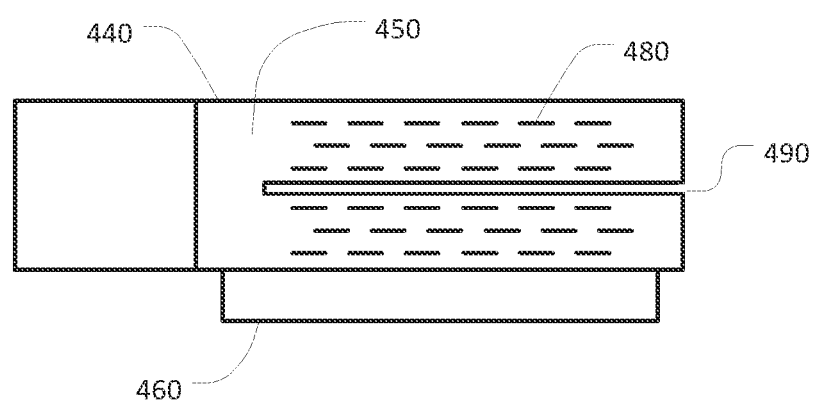

FIGS. 4A and 4B are simplified side and top views of a end effector 400 of a tool according to some embodiments. In some embodiments, end effector 400 is consistent with either or both of the jaws of end effector 220. As shown in FIGS. 4A and 4B, end effector 400 located at the distal end of tool 200 (e.g., end effector 220) includes a mechanism for jaw closure, tissue stapling, and tissue cutting similar to end effector 300 in FIGS. 3A and 3B. And although end effector 220 is shown and described with one fixed and one movable jaw, one of ordinary skill would understand that the distal end of tool 200 could be modified to use two movable jaws. It should be further understood that although the description below is in the context of a grasping, stapling, and cutting instrument that simultaneously grasps, staples, and cuts tissue, the aspects so described may be applicable to instruments with or without cutting features, instruments supporting fusing rather than stapling, and/or the like.

As shown in FIG. 4A, end effector 400 (similar to end effector 300) shows a cut-way side view of end effector 220 prior to actuation so that the jaws of end effector 220 are shown in an open position. As shown, end effector includes a first jaw 440 that is fixed and a second jaw 410 that is movable about a pivot point 430 near its proximal end. In the context of a stapling instrument, second jaw 410 may alternatively be referred to as anvil 410. In the embodiments shown in FIG. 4A, first jaw 440 further includes a first jaw surface 450 and second jaw 410 further includes a second jaw surface 420. As discussed herein, first jaw 440, second jaw 410, and pivot point 430 function the same or similar to first jaw 340, second jaw 310, and pivot point 430. However, as shown in FIGS. 4A and 4B, a different imaging sensor and system may be arranged on end effector 400 and utilized with end effector 220 to provide additional and/or different imaging configurations and processes.

In FIG. 4A, end effector 400 further includes a first imaging module 460 and a second imaging module 470 that collectively may constitute an imaging sensor that may capture images of a scene at or in proximity to end effector 400 during use, movement, and/or actuation of end effector 400, for example, images of a space and/or area between first jaw surface 450 and second jaw surface 420. First imaging module 460 and second imaging module 470 may correspond to a sensor package capable of capturing still images and/or video of a scene, which may be reflective imaging or trans-illumination imaging. In some embodiments, both first imaging module 460 and second imaging module 470 include detector sensor arrays configured to detect incoming radiation, such as a sensor array having one or more sensor pixels arranged in array or other fashion capable of detecting incident radiation on the sensor pixel. Thus, first imaging module 460 and second imaging module 470 may be capable of capturing visual images at or nearby tool 200 using visible light, such as the space/area between first jaw surface 450 and second jaw surface 420 in an open or closed position (e.g., before and/or after grasping a material respectively). In such embodiments, first imaging module 460 may correspond to a charge-coupled device (CCD) or complementary metal-oxide semiconductor (CMOS) image sensor. In some embodiments, first imaging module 460 and second imaging module 470 may also or instead include a thermal and/or infrared sensor that may be capable of capturing infrared images of the scene. In some embodiments, the pixels may capture an image at a point in time based on incoming radiation and/or may reconstruct an image over time based on movement of end effector 220 and the incoming radiation.

First imaging module 460 and second imaging module 470 may correspond to a single pixel wide array or narrow multiple pixel wide array of detector sensors that may detect incoming radiation incident on first imaging module 460 and second imaging module 470. First imaging module 460 and second imaging module 470 may run a length of first jaw 440 and second jaw 410, respectively, and/or may only run a portion of the length of their respective jaw. Moreover, first imaging module 460 and second imaging module 470 may each have separate and/or the same lengths. In some embodiments, one or more images (e.g., one or more of images 190) captured by first imaging module 460 and second imaging module 470 may correspond to separate images captured by their respective camera and displayed on an interface, or may be used to reconstruct an image, such as a three-dimensional reconstruction, of a material at and/or proximate to end effector 400 (e.g., between first jaw surface 450 and second jaw surface 420).

In some embodiments, the sensor package provided by first imaging module 460 and second imaging module 470 may provide trans-illumination imaging of radiation through a material. In such embodiments, one of first imaging module 460 and second imaging module 470 may correspond to a radiation emitter (e.g., an infrared emitted, ultraviolet emitter, and/or emitter of another wavelength and/or radiation type), while the other one of first imaging module 460 and second imaging module 470 may correspond to an infrared detector or other image sensor having pixels sensitive to infrared, ultraviolet, and/or another wavelength radiation (e.g., a pair of corresponding emitter and detector sensor pixel(s)). In such embodiments, moisture levels in a material, absorption, desiccation, and/or other property of the material may be determined using first imaging module 460 and second imaging module 470, as discussed below. In some embodiments, one of first imaging module 460 and second imaging module 470 may be a leaky fiber optic, such as a fiber optic bent at such a degree that light within the fiber exceeds the critical angle, escapes, and provides illumination, or a fiber optic that leaks light (e.g., a Corning® Fibrance® optical fiber). The other one of first imaging module 460 and second imaging module 470 may correspond to a sensing fiber, that may similarly be bent at angles sufficient to act as detectors from emitted light from the leaky fiber and/or may be a straight fiber optic similarly capable of sensing light. In such embodiments, the amount of returning light detected by the sensing fiber may be analyzed as discussed below.

Similar to imaging sensor 360, imaging using first imaging module 460 and second imaging module 470 on end effector 220 is accomplished by image control module 180 with imaging system 260 from the proximal end of end effector 220 exchanging electrical signals and/or the like with first imaging module 460 and second imaging module 470. Thus, one or more components of first imaging module 460 and second imaging module 470 are coupled to the one or more image delivery mechanisms 270. It should be further understood that although the description below is in the context of an image sensor instrument that captures visual images and/or infrared images, the aspects so described may be applicable to instruments with other types of sensors capable of capturing other types of radiation and/or the like. In some embodiments, first imaging module 460, second imaging module 470, and/or another component of end effector 400 (not shown) may also include an illumination and/or lighting system, as discussed in reference to FIGS. 3A and 3B. In such embodiments, an emitter may be located with, at, or proximate to first imaging module 460 and/or second imaging module 470 to provide the illumination. In some embodiments, the illumination emitter may be located on one or more of first jaw 440 and/or second jaw 410, or may be located elsewhere, such as on an endoscope associated with end effector 400 and located proximate to first imaging module 460 and/or second imaging module 470 so that illumination may be provided to the scene.

In FIG. 4B a second orientation of end effector 400 is shown, where a top down view of first jaw surface 450 of first jaw 440 is shown with a bottom up view of second jaw surface 420 of second jaw 410. In some embodiments, first imaging module 460 is located on or along a side of first jaw 440, such as running at least a portion of a length of a side of first jaw 440, and/or at an offset surface, flange, or area of first jaw 440 that allows first imaging module 460 to view, at an upward angle or degree, end effector 400 of end effector 220, such as a space and/or area between first jaw surface 450 and second jaw surface 420. Similarly, second imaging module 470 is located on and/or along a side of second jaw 410, such as running at least a portion of a length of a side of second jaw 410, and/or at an offset surface, flange, and/or area of second jaw 410 that allows second imaging module 470 to view, at a downward angle and/or degree, end effector 400 of end effector 220, such as the space or area between first jaw surface 450 and second jaw surface 420.

Thus, first imaging module 460 and second imaging module 470 may be parallel to an edge of their respective first jaw 440 and second jaw 410 that is capable of imaging at and/or around end effector 400, including the area and/or space between first jaw surface 450 and second jaw surface 420. First imaging module 460 is shown to be opposite second jaw 410 to allow for imaging of an area between first jaw 440 and second jaw 410, such as a material within an area between first jaw surface 450 and second jaw surface 420 that is captured and/or grasped. Similarly, second imaging module 470 is shown to be opposite first jaw 440 to allow for imaging of the same area. In some embodiments, first imaging module 460 and second imaging module 470 are located opposite as shown in FIG. 4b to allow for emission of radiation by one of first imaging module 460 and second imaging module 470 and detection of radiation by the other (e.g., visible or infrared light), but other configurations may be possible. This allows first imaging module 460 and second imaging module 470 to act as a emitter/detector pair that provides detection of material properties for materials between first imaging module 460 and second imaging module 470, as discussed below. It should be further understood that although the description below is in the context of an image sensor instrument at the side parallel edges of an end effector, the aspects so described may be applicable to instruments with other placements of an imaging sensor along a tool and/or at an end effector.

Additionally in FIG. 4B, first jaw 440 is designed to receive a replaceable staple cartridge holding a plurality of staples and a plurality of staple pushers. FIG. 4B shows a top view of first jaw surface 450 having six rows of staple slots 480 through which the staples may be applied to grasped tissue upon actuation of end effector 220 as described in reference to staple slots 370 in FIG. 3B and functioning the same or similar. FIG. 4B further shows a cutting slot 490 described in reference to cutting slot 380 in FIG. 3B and functioning the same and/or similarly.

In some embodiments, when imaging using first imaging module 460 and second imaging module 470, one or more images, such as one or more of images 190, may be captured of a space or an area between first jaw surface 450 and second jaw surface 420. The one or more images may correspond to visual images of the area or space, which may detect presence of material and other visible characteristics within the area by an imaging system (e.g., image control module 180 and/or imaging system 260). The area may correspond to an area that is graspable and/or grasped by first jaw 440 and second jaw 410 during use of end effector 220. Thus, the one or more images may be used to estimate and/or determine an amount of the area that is filled with material in the workspace (e.g., tissue of a patient when performing a grasping and/or stapling event during a medical use or operation). A percentage fill of the space or area between first jaw surface 450 and second jaw surface 420 may be approximated based on the visible material (e.g., tissue) between first jaw surface 450 and second jaw surface 420, such as a percentage occupancy of the material in the space between first jaw surface 450 and second jaw surface 420, similar to FIGS. 3A and 3B. Light may similarly be provided by an illumination system in conjunction with the imaging system.

In some embodiments, other types of images or image data may be captured, such as infrared images and/or data on transmission properties of material in the area and/or space between first imaging module 460 and second imaging module 470 (e.g., between first jaw surface 450 and second jaw surface 420). For example, trans-illumination infrared imaging may be utilized by first imaging module 460 and second imaging module 470 (e.g., through an emitter/detector pair formed by first imaging module 460 and second imaging module 470) to detect presence of water in tissue based on absorption of infrared light at certain wavelengths by an imaging system. The presence and/or amount of moisture detected by the imaging system between first jaw surface 450 and second jaw surface 420 may be utilized to determine the percentage fill of end effector 400 with material. In some embodiments, as the material is grasped and squeezed between first jaw surface 450 and second jaw surface 420 by end effector 400 during actuation of end effector 220, moisture (e.g., water) may be squeezed out of the material (e.g., tissue) causing desiccation. The presence and/or amount of moisture in the material may further be utilized by the imaging system to determine the percentage fill of the space or area with the material during the grasping action by end effector 220. The desiccation level during a grasping event determined through the one or more images may be used by the imaging system to determine a state of compression of the material, such as an amount of pressure applied and/or amount of compressed material.

In some embodiments, first imaging module 460 and second imaging module 470 may utilize specific wavelengths of light, such as at 1600 nm, 3500 nm, and/or another wavelength at which water absorbs and/or transmits light to determine the desiccation level of the material (e.g., the water content of the material). In such embodiments, by viewing the amount of light scene at each pixel, a water content and/or desiccation of the material may be determined. When utilizing more than one wavelength, such as a wavelength at which water absorbs and another wavelength where water transmits, the imaging system may utilize a ratio of detected radiation at each wavelength to more sensitively detect a presence of water or other fluid with a material. In some embodiments, first imaging module 460 may also be used to determine the presence of other fluids, such as blood or stomach fluid during a medical operation, which may be utilized to assist in actions by end effector 220 and diagnosis of issues within a workspace (e.g., a patient). In some embodiments, first imaging module 460 and second imaging module 470 may also be used to determine a fluorescence of a material using one or more wavelengths of light to determine material type, desiccation, and/or other property (e.g., 800 nm as in FIGS. 3A and 3B). Similar to FIGS. 3A and 3B, an imaging system (e.g., imaging system 260) may process the images using one or more modules (e.g., image control module 180) in order to determine the aforementioned properties.

In some embodiments, transmissivity (e.g., transmission level of radiation through a substance) of visible light through an area or space may also be utilized to detect presence of material between first imaging module 460 and second imaging module 470, as well as an amount and/or percentage fill of the area between first jaw surface 450 and second jaw surface 420. For example, when first imaging module 460 and second imaging module 470 correspond to an emitter/detector pair utilizing leaky fiber optics or other visible light pairs, the amount of detected and/or returning light in the detector of the emitter/detector pair may be used to determine properties of the material, including state of compression or pressure applied to the material, desiccation level or amount during an action by end effector 220, and the like. The imaging system may determine the transmission properties of the material utilizing such an imaging sensor pair, which may be analyzed for additional properties of the material by the imaging system.

As discussed above and further emphasized here, FIGS. 4A and 4B are merely examples which should not unduly limit the scope of the claims. One of ordinary skill in the art would recognize many variations, alternatives, and modifications. According to some embodiments, a relative size of the surface areas of the one or more of first jaw surface 450, second jaw surface 420, first imaging module 460, and/or second imaging module 470 may be different than as depicted in FIGS. 4A and 4B. According to some embodiments, the relative height, placement location, orientation, and/or field of vision of first imaging module 460 and/or second imaging module 470 may be different than as depicted in FIGS. 4A and 4B. In some examples, first imaging module 460 and/or second imaging module 470 may be flush with their respective one of first jaw 440 and second jaw 410 and/or recessed below their respective jaw. In some embodiments, an axial length (from proximal to distal) along end effector 400 of each of first imaging module 460 and/or second imaging module 470 may be longer, shorter, and/or of different lengths. Additionally, when discussed as an emitter/detector pair, it is understood that first linear imaging sensor 406 and second imaging module 470 may each function as the emitter and/or detector (e.g., are interchangeable depending on system requirements and functionality).

According to some embodiments, control of an end effector, such as end effector 220, that supports both grasping (e.g., using opposing jaws) and image capture and delivery (e.g., using first imaging module 460) are typically controlled using separate systems. For example, a drive system and a corresponding grasp control module may control the grasping while an imaging system and a corresponding image control module may control the image capture, delivery, and processing. In some examples, there may be little or no cooperation between drive system/grasp control module and the imaging system/image control module. That is, the drive system/grasp control module may control grasping based on mechanical and/or kinematic properties of the grasped material and not the material and spatial occupancy properties of the grasped material that indicate whether grasping, sealing, and/or cutting are occurring satisfactorily. Similarly, the imaging system/image control module may control imaging and image display based on material and spatial occupancy properties of the grasped material and not the mechanical and/or kinematic properties of the material that indicate whether a grasp of the material that is likely to result in good grasping, sealing, and/or cutting has been obtained. Accordingly, better sealing and cutting of a grasped material may be obtained when the drive system/grasp control module and the imaging system/image control module work together to control both the grasping and imaging so that both the grasping and imaging work to complement each other.

Figure 5:
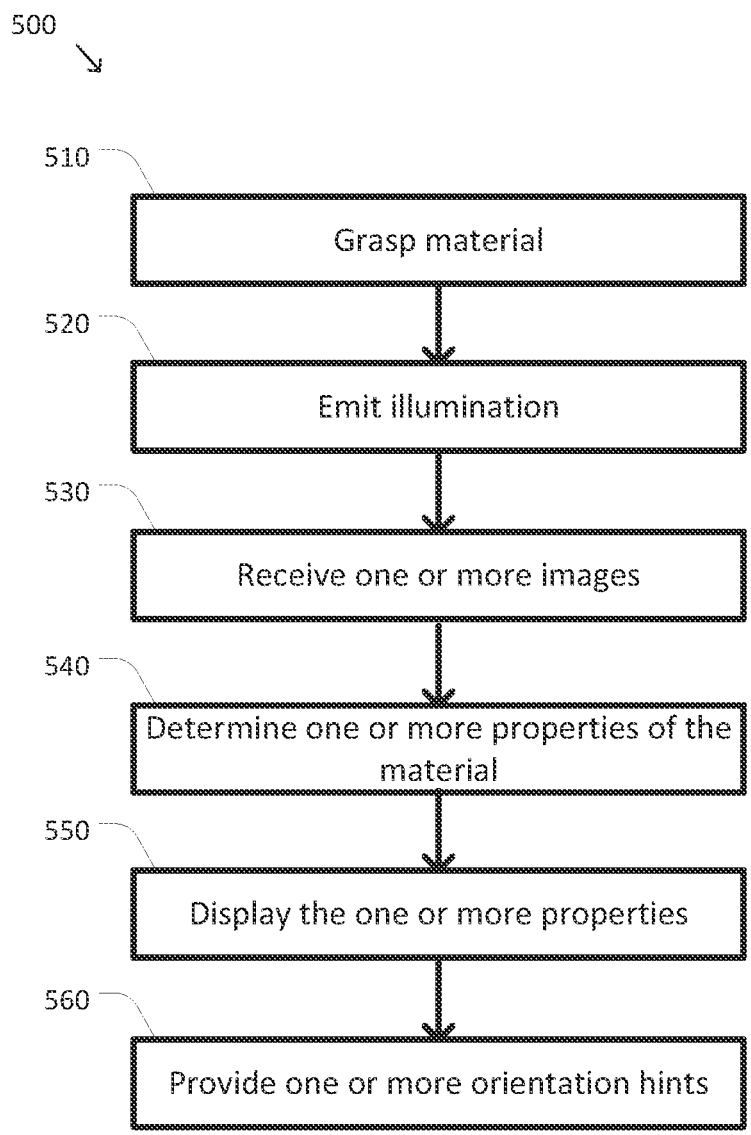
FIG. 5 is a simplified diagram of a method for material manipulation according to some embodiments.

FIG. 5 is a simplified diagram of a method 500 for grasping and energy delivery according to some embodiments. One or more of the processes 510-560 of method 500 may be implemented, at least in part, in the form of executable code stored on non-transitory, tangible, machine readable media that when run by one or more processors (e.g., the processor 150 in control unit 140) may cause the one or more processors to perform one or more of the processes 510-560. In some embodiments, method 500 may be performed by one or more modules, such as grasp control module 170 and/or image control module 180. In some embodiments, portions of method 500 associated with grasping (e.g., sensing of mechanical and/or kinematic information and mechanical control of grasping jaws) may be performed by grasp control module 170 and portions of method 500 associated with image capture and analysis (e.g., capturing, recording, and analyzing images for determination of material presence and properties) may be performed by image control module 180 with grasp control module 170 and image control module 180 cooperating to share sensor and control information so as to optimize image capture with a grasped or graspable material. In some embodiments, process 560 is optional and may be omitted, or may be performed prior to one or more of processes 510, 520, 530, 540, and/or 550. In some embodiments, method 500 may be performed in a different order than the order implied by FIG. 5. In some examples, processes 520, 530, 540, 550, and 560 may be performed before process 510 and/or processes 520, 530, 540, 550, and 560 may be performed concurrently with process 510. In some examples, process 520 is optional and may be omitted as necessary. In some embodiments, both processes 520 and 530 may occur concurrently.

At a process 510, a material is grasped. In some examples, the material may be grasped between the jaws of an end effector, such as end effector 220. In some examples, the end effector may be consistent with end effector 300 and/or end effector 400. In some examples, the material may be grasped using a drive system, such as drive system 240, under the control of a grasp control system, such as grasp control module 170. In some examples, the grasp may occur based on a command received from an operator. In some examples, the grasp may include actuation of the jaws until a desired angle between the jaws is reached, a desired separation between the jaws is reached, and/or a desired force or torque limit indicating a desired grasp strength is reached. In some examples, the grasp may actuate the jaws to a desired position set point (e.g., a desired angle and/or separation between the jaws) subject to an upper force and/or torque limit. In some examples, the force or torque limits may be implemented as a current limit on the one or more actuators used to actuate the jaws.

At a process 520, illumination is emitted. Illumination may be provided to a scene at or nearby the distal end of tool 200 where end effector 220 is currently operating within a workspace. In some examples, end effector 220 is part of a medical tool utilized inside a patient, and may correspond to a grasping, sealing (e.g., stapling), and/or cutting tool with the material grasped at process 510. Thus, illumination may be provided to the tissue of a patient that is proximate to end effector 220. Illumination may be provided by an illumination system that includes a LED, other diode, light pipe, fiber optic, and/or light emission device at or nearby the distal end of tool 200 and nearby end effector 220 (e.g., located at and/or nearby imaging sensor 360 or first and second linear imaging sensors 460/470). The illumination may consist of visible light, and/or may be other radiation including infrared radiation. In some embodiments, illumination may be provided by another or an additional articulating arm or tool, for example, provided a different end effector.

In some embodiments, illumination may be provided by one or more optical fibers that span a distance from a light source and illumination control system at the proximal end of tool 200 to the illuminating device at the distal end of the tool and nearby end effector 220. The optical fibers may be combined with drive mechanisms 250 and/or image delivery mechanisms 270 through an arm and other components of tool 200. The light or illumination source at the proximal end of tool 200 may correspond to a light engine having red, green, and blue LEDs and/or laser diodes that may mix to create colored/white light, a white LED, an infrared light source, an ultraviolet light source, and/or the like. In some embodiments, the illumination control system may be controlled by one or more of grasp control module 170 and image control module 180.

In some embodiments, the one or more of the illumination control system, grasp control module 170, and image control module 180 may also control ambient increases in temperature caused by providing light to the scene. This may prevent overheating of sensitive material caused by the illumination. Thus, end effector 220 and/or another component of tool 200 may also include a temperature measurement component (e.g., thermometer, thermocouples, thermal resistors, thermistor, etc.) located on and/or near one or both of the jaws that may measure temperature at and/or near the scene and provide feedback of illumination correction. In some examples, the temperature of the grasped material may be determined using an infrared sensor, such as an imaging sensor that may further be used to capture one or more images discussed below. The one or more systems may then adjust illumination and/or turn off illumination as necessary. However, in other embodiments, temperature change by the illumination may be unimportant (e.g., during heating events by end effector 220).

At a process 530, one or more images are received. Image capture and receipt may be performed by an imaging system, such as imaging system 260, which may be controlled by an image control module, such as image control module 180. In some examples, imaging and receipt of the one or more images may occur based on a command received from an operator, and/or may occur automatically based on an interaction with drive system 240 under the control of grasp control module 170 when grasping a material in a workspace.

In some embodiments as shown in FIGS. 3A and 3B, the one or more images may be received from a single imaging sensor, such as imaging sensor 360, located at or near a distal tip of tool 200, such as near a distal tip of end effector 300 (e.g., either the tip of first jaw 340 or second jaw 310). In such embodiments, the one or more images may be captured from a single sensor and transmitted to imaging system 260 and/or image control module 180 from imaging sensor 360. In other embodiments as shown in FIGS. 4A and 4B, the one or more images may be received from an imaging module, such as first imaging module 460 and second imaging module 470 that are located in opposing positions along end effector 400, such as at the sides of first jaw 440 and second jaw 410, respectively. In such embodiments, the one or more images may correspond to a plurality of images and/or one or more combined images using the two or more imaging modules.

In some embodiments, the one or more images may correspond to visual images captured using visible light. Such images may therefore include a visual representation of a scene, which may include objects in the scene, such as a material within a workspace. Thus, the one or more images may correspond to visual data shown in a visual representation of a scene using visual light (e.g., through reflective imaging and detection of visual light by one or more imaging sensors).

In some embodiments, the one or more images may include infrared image data, transmission data of light and/or other radiation through a material, and the like. In such embodiments, the images may therefore include additional information, such as amount of visible/infrared light absorbed or transmitted through a material or liquid associated with the material and/or absorption of the light emitted from the emitter and detected by the detector (e.g., an amount or percentage of the emitted light that is detected by the detector). The one or more images may include data of emitted light wavelength(s) for use during processing and transmission/absorption data of the emitted light. Thus, the one or more images may include image data detected of trans-illumination, scene fluorescence, and/or the like for the material located in the scene.

At a process 540, one or more properties of the material captured in the one or more images are determined. The one or more images may correspond to image data of a scene, which includes data of the material captured using one or more imaging sensors located on and/or near end effector 220. As discussed above, the image data may correspond to visual image data, such as detected visual light that is radiant, transmissive (e.g., during trans-illumination), fluorescent, and/or reflective from and/or through a material in a scene, and/or may correspond to detection of other types of radiation in a scene. In addition to the below properties determined from one or more images, changes to the properties may also be determined, for example, when utilizing a plurality of images and/or video.

In some examples, the one or more properties may be determined from one or more images obtained from an imaging sensor of the jaws and the grasped or graspable material. Thus, the one or more properties may be used to determine a presence and/or absence of a material in a scene as well as the material within an area and/or space between the articulating jaws of end effector 220 (e.g., first jaw 340/440 and second jaw 310/410). In some embodiments, the one or more images may also be used to determine a length and/or amount of fill of the area/space between the jaws, for example, by detecting a length, width, and/or height of the material entering and occupying the jaws.

In some examples, the one or more properties may include a desiccation level (e.g., moisture content) of the grasped and/or graspable material. In some examples, the desiccation level may provide an indicator of a level of current material sealing, an indication of whether the material is ready for cutting and/or sealing (e.g., it may be advantageous to squeeze moisture out the material by grasping before cutting and/or sealing). In some examples, the desiccation level may be determined from the moisture and/or water levels prior to and/or after grasping and clamping by end effector 220. In some examples, the desiccation level may be determined based on the presence and amount of water in the tissue prior to and/or after grasping the material utilizing light. For example, at certain wavelengths (e.g., approximately 1600 nm and/or 3500 nm), light is significantly absorbed by water. Thus, utilizing light at this wavelength with the material allows a determination of water content within a material. In some embodiments, multiple light wavelengths, such as a wavelength at which water absorbs and another wavelength at which it water transmits the light, may be utilized to detect the presence and amount of water with more sensitivity and/or accuracy. In some embodiments, light at 800 nm may cause fluorescence of liquid (e.g., a fluorescing compound, such as indocyanine green and/or the like) from a material to determine the material's desiccation level.

In some examples, the state of compression, stiffness, and/or pressure applied to the grasped material may be determined using the one or more images, as well as other determined properties. In some examples, the desiccation level may be used to determine the state of compression. In some examples, the stiffness and/or state of compression of the grasped material may be determined from the jaw angle and/or separation. In some examples, a type of fluid, fluorescence of the fluid and/or material, trans-illumination of light through the fluid or material, and/or absorption of light by the fluid or material may be determined using the one or more images.

In some embodiments, at process 540, additional data may be determined, such as a percentage fill of the jaws of end effector 220 (e.g., an amount or percentage that the space/area between first jaw 340/440 and second jaw 310/410 is filled prior to grasping a material and/or after grasping a material). In some embodiments, the percentage of the area/space filled with the material may be determined from visual image data, such as the presence and length/amount of material between the jaws. In some embodiments, the percentage (or other measurement) may be determined based on desiccation level information for the material prior to grasping or when grasped by the jaws. For example, when applying pressure to a material, liquid (e.g., water) may be squeezed out of the material. Based on the amount of water desiccated from the material (e.g., before and/or after grasping), the percentage of the area/space may be determined.

At a process 550, the one or more properties are displayed. The one or more properties may be displayed on an interface of a device or machine associated with tool 200, such as one in connection with control unit 140 that may display data used for operation of device 110 and tool 200 within a workspace. The one or more properties may be displayed with the one or more images, and/or may be displayed independent of the one or more images. Additionally, the one or more properties may be displayed with additional data that caused the one or more properties, such as a clamping pressure and/or state of compression of a material, a desiccation level of the material, and/or other data determined from the one or more images during process 540. Where the one or more properties include specific data for portions, areas, and/or points within the workspace and/or on the material, the properties may be displayed with those locations and/or used to identify those locations. In some embodiments, the one or more properties may also be displayed with instructions to operate and/or move tool 200 and/or end effector 220 in order to properly operate tool 200 and/or end effector 220 within the workspace. For example, where the one or more properties correspond to a percentage fill of a space and/or area between two jaws on end effector 220, the one or more properties may be displayed with instructions to grasp more or less of the material (e.g., movement directions, grasping and/or release directions, etc.). The data can also be used to control the end effector, e.g. adjusting the clamping force based on percentage fill. In some embodiments, feedback from one or more sensors on end effector 220 may be used within a closed loop control of end effector 220. The feedback may be used to adjust a property or usage of end effector 220, such as by adjusting pressure or force imparted by end effector 220 onto the material within or graspable by end effector 220.

In some embodiments, display of the one or more images with the one or more properties may occur in a picture-in-picture, separate view pane, off-to-side view, and/or over the jaws and/or other part of end effector 220 in order to provide context to the images. Moreover, at process 550, in some embodiments, video stabilization may be applied during capture of video data. The video stabilization may fix particular points on the material to locations within an interface to provide a stabilized frame of reference. In some embodiments, additional types of video stabilization may be applied.

At an optional process 560, one or more orientation hints are provided. In some embodiments, the one or more orientation hints may be determined relative to end effector 220 in a workspace so that an orientation of the one or more images captured during process 530 relative to end effector 220 and/or the jaws of end effector 220 that may be captured by a separate imaging device, such as an endoscope used to capture images of end effector 220 and/or a workspace around end effector 220, thereby displaying an orientation of the one or more images captured during process 530. In some embodiments, the orientation hints may correspond to an image, graphic, and/or animation within images of the workspace, such as a T-pose of a body in a prone position with arms of the body that are perpendicular to a horizontal axis of the body (e.g., the chest and legs) with the face of the body showing the direction of view and/or view up for the images captured during process 530. In some embodiments, the orientation hints may also show movement of the end effector within the workspace.

In some embodiments, the orientation hints may be animated to display a "fly-in" or movement of end effector 220 as it enters and moves within the workspace along its various DOFs. As such, the orientation hints may be determined based on inputs and/or automatic movements of tool 200 as it enters and is used within the workspace. In other embodiments, the orientation hints may be fixed to show a current position and/or orientation of the one or more images captured during process 530 and/or may be animated to show how the position and/or orientation of the one or more images may have been captured over time. In some embodiments, when providing the one or more orientation hints, an animation of the one or more orientation hints may be utilized prior to, with, and/or after display of the one or more images, which may occur through the interface. In some embodiments, the animation of the one or more orientation hints (e.g., T-pose of a prone body) may start in an upper left corner of the interface and proceed to the lower right corner of images showing the workspace and then displaying the one or more images for proper orientation of the one or more images within the workspace relative to the view of the workspace as shown in the images captured by the endoscope.

In some embodiments, the orientation hints may provide hints for up, down, left, right, one or more cardinal directions, or other directional hint within the workspace, which may be determined based on inputs/movements of tool 200 as well as other sensors (e.g., a gravity sensor, compass, etc.). The one or more orientation hints may be further determined and output as described below.

Figure 6A:
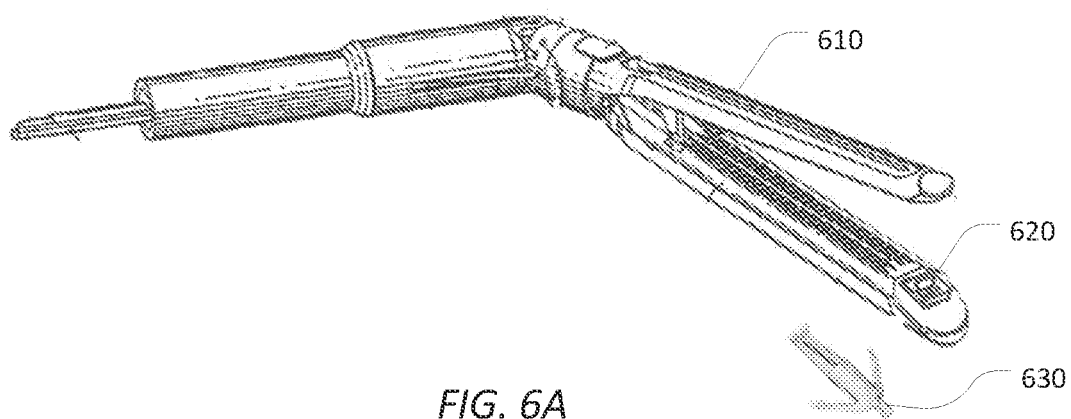
FIGS. 6A, 6B, and 6C are simplified orientation view hints for an interface of a computer-assisted system of FIG. 1 having an end effector of FIGS. 3A and 3B or FIGS. 4A and 4B according to some embodiments.
Figure 6B:
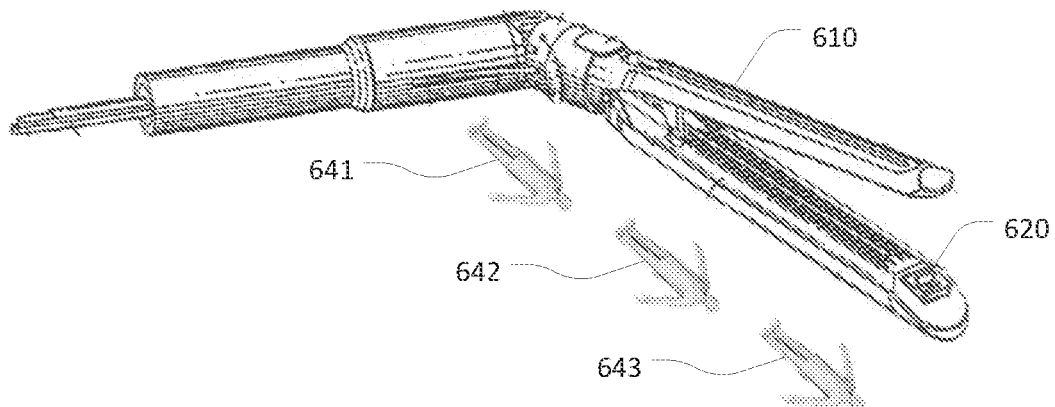
Figure 6C:
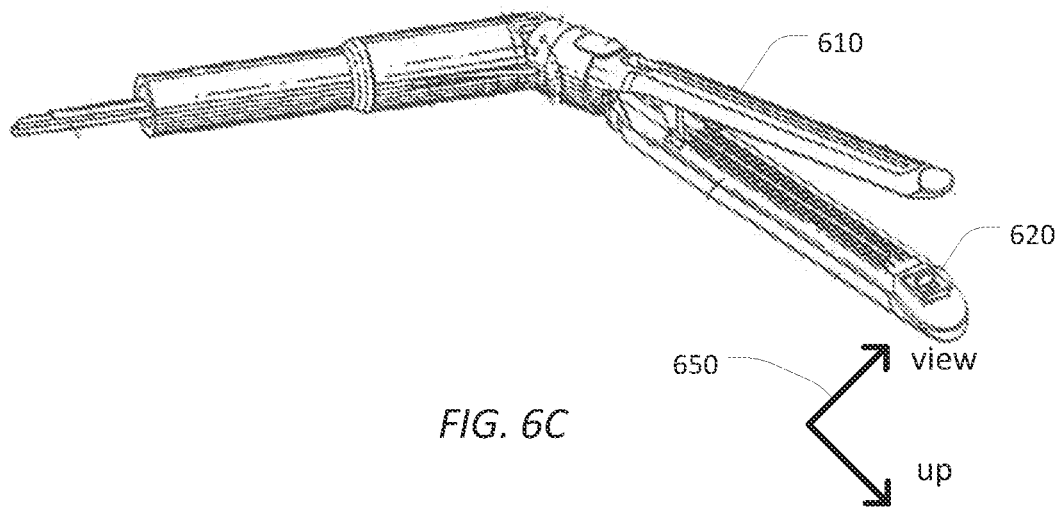

FIGS. 6A, 6B, and 6C are simplified orientation view hints for an interface of a computer-assisted system of FIG. 1 having an end effector of FIGS. 3A and 3B or FIGS. 4A and 4B according to some embodiments. FIGS. 6A-C display an exemplary interface display when displaying orientation hints during use of a tool within a workspace, such as the orientation hints discussed in reference to process 560 of method 500. In some embodiments, FIGS. 6A-6C show images of an end effector 610, such as might be captured by an imaging device located in the workspace (e.g., an endoscope mounted to another repositionable arm). In some examples, end effector 610 may correspond to end effector 220, end effector 300, and/or end effector 400 that is utilized within a workspace, and may include an imaging sensor 620 that may correspond to imaging sensor 360, first imaging module 460, and/or second imaging module 470 as described in further detail above. However, the visual representation of end effector 610 and/or imaging sensor 620 within an interface may also be different in some embodiments. In some examples, imaging sensor 620 may be consistent with imaging sensor 360, first imaging module 460, and/or second imaging module 470.

As shown in FIG. 6A, an orientation hint 630 is provided in the form of a still T-pose of a prone body. The position and/or orientation of orientation hint 630 provides hints to the operator as to the orientation of the one or more images captured by imaging sensor 620 in relation to the view of end effector 610 being displayed to the operator as part of FIG. 6A. Thus, orientation hint 630 provides context to the operator regarding the direction of view and/or the view up direction for the one or more images captured by imaging sensor 620.

In some examples, end effector 610 and/or imaging sensor 620 may be hidden from view of the operator during the operation, such as by material and/or tissue grasped by end effector 610. In order to provide context and orientation of a view captured by imaging sensor 620 when located on end effector 610, a direction of the view and/or of view up of imaging sensor 620 relative to the workspace in the images captured by the endoscope may be displayed using orientation hint 630 on an interface. The direction of view up on orientation hint 630 may be provided by rotating and/or orienting the head of the T-pose figure in orientation hint 630 so that the face is directed in the direction of view and the top of the head is towards view up. Thus, orientation hint 630 when providing a view up orientation may be shown based on the facial direction of the T-pose body relative to the view of end effector 610 provided in the view corresponding to FIG. 6A. In some embodiments, the one or more images captured by imaging sensor 620 may be provided as a picture-in-picture image next to the images of end effector 610, imaging sensor 620, and/or orientation hint 630.

As shown in FIG. 6B, an animation of orientation hints 641, 642, and 643 may be used to provide a visual representation of the view direction and/or view up orientation of view of imaging sensor 620 relative to the workspace, as discussed above. In FIG. 6B, the animation may move an orientation hint from locations corresponding to orientation hint 641, 642, and 643. In some examples, the animation may move the orientation hints from top left corner to bottom right corner of the interface, based on previous motion of end effector 610 within the workspace, and/or the like. In some examples, orientation hints 641-643 may be different or separate so as to show an animation of different workspace poses and/or directions.

As shown in FIG. 6C, an orientation hint 650 may also display one or more relative directions of view up or another view, or may instead utilize cardinal directions and the like, to provide an orientation hint for a current direction of imaging sensor 620 and/or a view up direction of imaging sensor 620. For example, orientation hint 650 displays the direction of view as a "view" arrow and a view up direction as an "up" arrow. In some examples, orientation hint 650 may be animated similar to the T-pose orientation hint as shown in FIG. 6B.

Figure 7A:
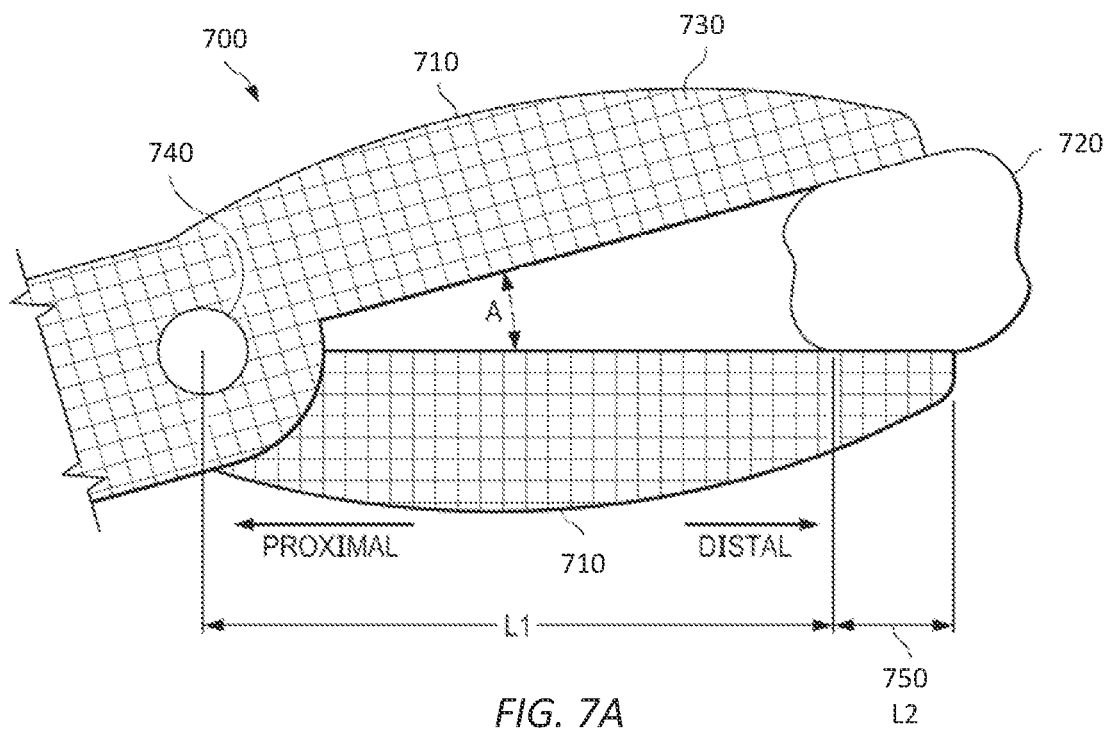
FIGS. 7A and 7B are simplified diagrams of the distal end of an instrument grasping a material according to some embodiments.
Figure 7B:
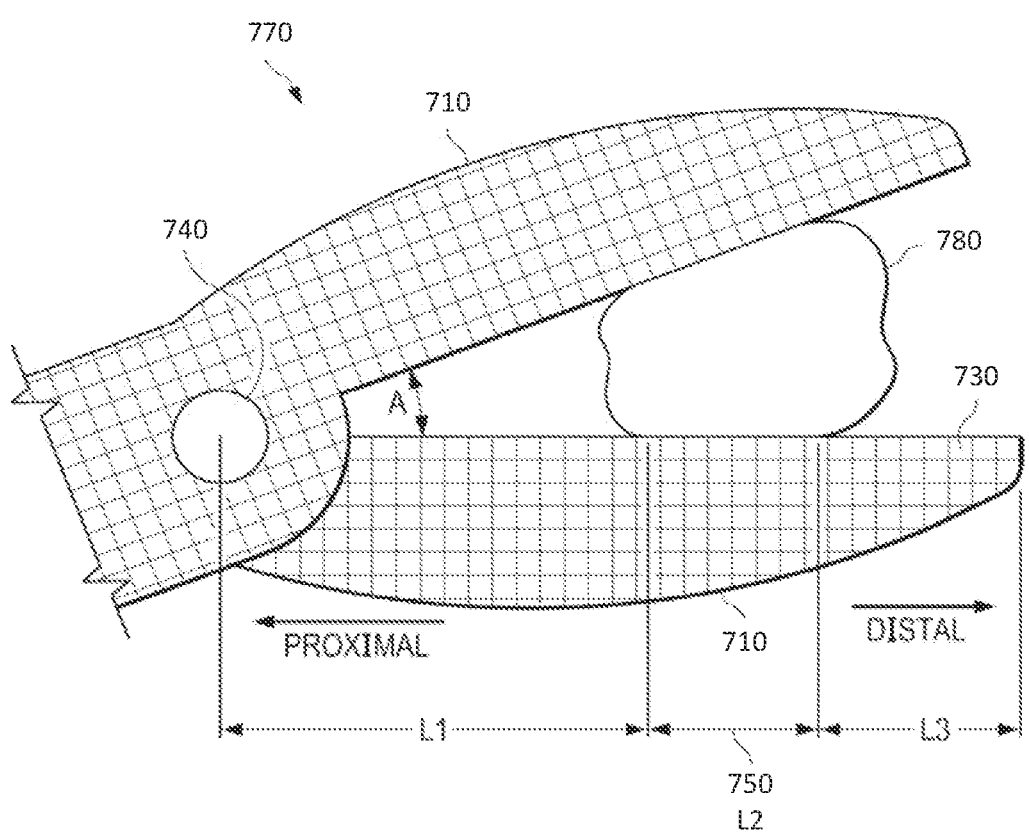

FIGS. 7A and 7B are simplified diagrams of the distal end of an instrument grasping a material according to some embodiments. In some examples, FIGS. 7A and 7B depict images 700 and 770 shown as informational for the description of FIGS. 7A and 7B. Thus, FIGS. 7A and 7B present an exemplary scenario meant for the discussion of a percentage fill of jaws 730, which may be captured with other perspectives and data by imaging sensor 620, imaging sensor 360, first imaging module 460, and/or second imaging module 470. In this regard, images 700 and 770 may correspond to descriptive images of an end effector 710, such as end effector 220, where an imaging sensor may capture other images of a material graspable by the end effector, and the side-view of end effector 710 during operation as shown in FIGS. 7A and 7B are exemplary to discuss operation of end effector 710 with an imaging sensor to determine a percentage fill of end effector 710 with a material. As shown in FIG. 7A, a material 720, such as tissue, may be grasped by jaws 730 toward the distal end of the jaws 730. As further shown in FIG. 7A, a grasping zone 750 at a distal end of jaw 730 may indicate where jaws 730 and the material 720 are in contact. Additionally, a length L1 indicates a distance between a proximal end 740 of jaws 730 and a proximal end of the grasping zone 750.

Similarly, as shown in image 770 of FIG. 7B, a material 780, which may be similar to the material 720, may be grasped by jaws 730. As further shown in FIG. 7B, a grasping zone 750 may indicate where jaws 730 and the material 780 are in contact. Again, a length L1 indicates a distance between the proximal end 740 of jaws 730 and a proximal end of the grasping zone 750. Additionally, a length L3 indicates a distance between a distal end of the grasping zone 750 and a distal end of jaw 730. As shown in FIG. 7B, the grasping zone 750 is in between the length L1 and L3. Also, the length L1 in FIG. 7A may be greater than the length L1 in FIG. 7B and the angle A between the jaws 730 in FIG. 7A may be smaller than the angle A between jaws 730 in FIG. 7B even when the material 720 and 780 have substantially the same size and/or shape. In some embodiments, imaging sensor 360 and/or first imaging module 460 with second imaging module 470 may operate to capture L1, L2, and/or L3 by determining an amount of material 720 that enters grasping zone 750 and/or an amount of material 720 and/or 780 within grasping zone 750. In some examples, imaging sensor 360 may monitor, over time, an amount of a material as it enters jaws 730 and in combination with known information about motion of end effector 220 may be used to determine grasping zone 750 to determine L1, L2, and/or L3, or may image part or all of grasping zone 750 having material 720 and/or or 780 within grasping zone 750 for the determination, such as with reflective light and/or radiation. In some embodiments, first imaging module 460 with second imaging module 470 may similarly image the area using transmissive light through material 720 and/or 780 and determine grasping zone 750 by detecting where light and/or radiation emitted from one of first imaging module 460 and second imaging module 470 is received by the other one of the modules and/or where light and/or radiation emitted by first imaging module 460 and/or second imaging module 470 is reflected back to first imaging module 460 and/or second imaging module 470, respectively. In some embodiments, the percentage fill may also be determined by imaging sensor 360 and/or first imaging module 460 with second imaging module 470 through material characteristics, such as a desiccation level, transmissivity of radiation through material 720 and other space of grasping zone 750, fluorescence of material 720 and/or 780, and/or absorption of radiation by material 720 and/or 780.

In some embodiments, a percentage fill of jaws 730 is determined based on one or more of the length L1, L2, L3, and/or the like. In some embodiments, a percentage fill P1 of material 720 between jaws 730 in FIG. 7A may be determined as a function of L2/(L1+L2). Thus, in FIG. 7A, P1=L2/(L1+L2). In some embodiments, the percentage fill P2 of jaws 730 in FIG. 7B with material 720 may be determined as a function of L2/(L1+L2+L3) to include the region L3 that does not include graspable material after material 780 is placed further within jaws 730. Thus, in FIG. 7B, P2=L2/(L1+L2+L3). In some embodiments, the functions P1 and P2 additionally depend on "other parameters" such as a procedure to be performed on the material, a material type, other material properties (e.g., desiccation, etc.), an operator preference, a position and/or orientation of the instrument or end effector 710, and/or the like and therefore a number of lookup tables are composed based on the other parameters and are stored in memory.

Some examples of control units, such as control unit 140 may include non-transitory, tangible, machine readable media that include executable code that when run by one or more processors (e.g., processor 150) may cause the one or more processors to perform the processes of method 500. Some common forms of machine readable media that may include the processes of method 500 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A computer-assisted device comprising:
an end effector having a first jaw and a second jaw;
an imaging sensor mounted to the first jaw or the second jaw and configured to capture one or more images of a material graspable by the first jaw and the second jaw; and
one or more processors coupled to the end effector and the imaging sensor, the one or more processors being configured to:
receive the one or more images from the imaging sensor;
analyze the one or more images to determine a length of a space between the first jaw and the second jaw filled with the material; and
display, on a user interface, information describing the length of the space between the first jaw and the second jaw filled with the materials.

2. The computer-assisted device of claim 1, wherein the end effector further comprises one or more of:
a stapling mechanism configured to staple the material; or
a cutting mechanism configured to cut the material.

3. The computer-assisted device of claim 1, wherein the imaging sensor is mounted to a side of the first jaw or a side of the second jaw.

4. The computer-assisted device of claim 1, wherein the one or more processors are further configured to display, on the user interface, the one or more images of the material.

5. The computer-assisted device of claim 1, wherein the one or more processors are further configured to:
analyze the one or more images to determine at least one of a width of the material or a height of the material; and
display, on the user interface, at least one of the width of the material or the height of the material.

6. The computer-assisted device of claim 1, wherein the one or more processors are further configured to:
analyze the one or more images to determine a percentage of the space between the first jaw and the second jaw filled by the material; and
display, on the user interface, the percentage of the space between the first jaw and the second jaw filled by the material.

7. The computer-assisted device of claim 6, wherein the one or more processors are configured to determine the percentage of the space between the first jaw and the second jaw filled by the material using a function based on at least one of a procedure to be performed on the material, a type of the material, an operator preference, a position of the end effector, or an orientation of the end effector.

8. The computer-assisted device of claim 1, wherein the one or more processors are further configured to analyze the one or more images to determine a grasping zone indicating where the material is in contact with at least one of the first jaw or the second jaw.

9. The computer-assisted device of claim 8, wherein to determine the grasping zone, the one or more processors are configured to:
determine a first distance between the material and a proximal end of the first jaw or the second jaw; and
determine a second distance between the material and a distal end of the first jaw or the second jaw.

10. The computer-assisted device of claim 1, wherein the one or more processors are further configured to analyze the one or more images to determine at least one of:
a desiccation of the material;
a change in the desiccation of the material;
a pressure applied to the material by the first jaw and the second jaw;
a change in the pressure applied to the material;
a transmissivity of the material captured in the one or more images;
a change in the transmissivity of the material;
an absorption of a liquid by the material;
a change in the absorption of the liquid by the material;
a fluorescence of the material captured in the one or more images; or
a change in the fluorescence of the material.

11. A method comprising:
operating, by one or more processors, an end effector having a first jaw and a second jaw;
capturing, by the one or more processors using an image sensor mounted to the first jaw or the second jaw, one or more images of a material grasped by the first jaw and the second jaw;
analyzing, by the one or more processors, the one or more images to determine a length of a space between the first jaw and the second jaw filled with the material; and
displaying, by the one or more processors on a user interface, information describing the length of the space between the first jaw and the second jaw filled with the material.

12. The method of claim 11, further comprising displaying, by the one or more processors on the user interface, the one or more images of the material.

13. The method of claim 11, further comprising:
analyzing, by the one or more processors, the one or more images to determine at least one of a width of the material or a height of the material; and
displaying, by the one or more processors on the user interface, at least one of the width of the material or a height of the material.

14. The method of claim 11, further comprising:
analyzing, by the one or more processors, the one or more images to determine a percentage of the space between the first jaw and the second jaw filled by the material; and
displaying, by the one or more processors on the user interface, the percentage of the space between the first jaw and the second jaw filled by the material.

15. The method of claim 11, further comprising analyzing, by the one or more processors, the one or more images to determine a grasping zone indicating where the material is in contact with at least one of the first jaw or the second jaw.

16. The method of claim 15, wherein determining the grasping zone comprises:
determining a first distance between the material and a proximal end of the first jaw or the second jaw; and
determining a second distance between the material and a distal end of the first jaw or the second jaw.

17. A non-transitory machine-readable medium comprising a plurality of machine-readable instructions which when executed by one or more processors are adapted to cause the one or more processors to perform a method comprising:
operating an end effector having a first jaw and a second jaw;
capturing, using an image sensor mounted to the first jaw or the second jaw, one or more images of a material grasped by the first jaw and the second jaw;

analyzing the one or more images to determine a length of a space between the first jaw and the second jaw filled with the material; and displaying, on a user interface, information describing the length of the space between the first jaw and the second jaw filled with the material.

18. The non-transitory machine-readable medium of claim 17, wherein the method further comprises displaying, on the user interface, the one or more images of the material.

19. The non-transitory machine-readable medium of claim 17, wherein the method further comprises:

analyzing the one or more images to determine a percentage of the space between the first jaw and the second jaw filled by the material; and displaying, on the user interface, the percentage of the space between the first jaw and the second jaw filled by the material.

20. The non-transitory machine-readable medium of claim 17, wherein the method further comprises analyzing the one or more images to determine a grasping zone indicating where the material is in contact with at least one of the first jaw or the second jaw.

\* \* \* \* \*